United States Patent
Yuen et al.

(10) Patent No.: US 9,374,279 B2
(45) Date of Patent: *Jun. 21, 2016

(54) MOTION-ACTIVATED DISPLAY OF MESSAGES ON AN ACTIVITY MONITORING DEVICE

(71) Applicant: Fitbit, Inc., San Francisco, CA (US)

(72) Inventors: Shelten Yuen, Berkeley, CA (US); Timothy Roberts, San Francisco, CA (US)

(73) Assignee: Fitbit, Inc., San Francisco, CA (US)

( * ) Notice: Subject to any disclaimer, the term of this patent is extended or adjusted under 35 U.S.C. 154(b) by 2 days.

This patent is subject to a terminal disclaimer.

(21) Appl. No.: 14/580,808

(22) Filed: Dec. 23, 2014

(65) Prior Publication Data

US 2015/0113417 A1    Apr. 23, 2015

Related U.S. Application Data

(60) Continuation of application No. 14/271,389, filed on May 6, 2014, now Pat. No. 8,954,290, which is a continuation-in-part of application No. 13/959,714, filed on Aug. 5, 2013, now Pat. No. 8,762,101, which (Continued)

(51) Int. Cl.
*G06F 3/00* (2006.01)
*A61B 5/00* (2006.01)
(Continued)

(52) U.S. Cl.
CPC .............. *H04L 41/22* (2013.01); *A61B 5/0022* (2013.01); *A61B 5/1118* (2013.01); *G06F 1/163* (2013.01);

(Continued)

(58) Field of Classification Search
CPC . G01C 22/006; A61B 5/1118; A63B 24/0062
USPC .................................................. 702/150, 160
See application file for complete search history.

(56) References Cited

U.S. PATENT DOCUMENTS 2,717,736 A    9/1955    Schlesinger
2,827,309 A    3/1958    Fred
(Continued)

FOREIGN PATENT DOCUMENTS

JP    11347021 A    12/1999
RU    2178588 C1    1/2002
(Continued)

OTHER PUBLICATIONS

A Hybrid Discriminative/Generative Approach for Modeling Human Activities, Lester, et al., Proc. of the Int'l Joint Conf. Artificial Intelligence, 2005, pp. 766-772.

(Continued)

*Primary Examiner* — Gregory J Toatley
*Assistant Examiner* — Michael Dalbo
(74) *Attorney, Agent, or Firm* — Martine Penilla Group, LLP

(57) ABSTRACT

Methods, systems and devices are provided for motion-activated display of messages on an activity monitoring device. In one embodiment, method for presenting a message on an activity monitoring device is provided, including the following method operations: storing a plurality of messages to the activity monitoring device; detecting a stationary state of the activity monitoring device; detecting a movement of the activity monitoring device from the stationary state; in response to detecting the movement from the stationary state, selecting one of a plurality of messages, and displaying the selected message on the activity monitoring device.

27 Claims, 16 Drawing Sheets

Related U.S. Application Data is a continuation-in-part of application No. 13/693,334, filed on Dec. 4, 2012, now Pat. No. 8,548,770, which is a division of application No. 13/667,229, filed on Nov. 2, 2012, now Pat. No. 8,437,980, which is a division of application No. 13/469,027, filed on May 10, 2012, now Pat. No. 8,311,769, which is a division of application No. 13/246,843, filed on Sep. 27, 2011, now Pat. No. 8,180,591, which is a division of application No. 13/156,304, filed on Jun. 8, 2011, now Pat. No. 9,167,991, said application No. 13/959,714 is a continuation-in-part of application No. 13/759,485, filed on Feb. 5, 2013, now Pat. No. 8,543,351, which is a division of application No. 13/667,229.

(60) Provisional application No. 61/388,595, filed on Sep. 30, 2010, provisional application No. 61/390,811, filed on Oct. 7, 2010.

(51) Int. Cl.
| | |
|---|---|
| *H04L 12/24* | (2006.01) |
| *G06F 3/01* | (2006.01) |
| *G06F 17/21* | (2006.01) |
| *H04L 29/08* | (2006.01) |
| *H04W 4/20* | (2009.01) |
| *G06F 1/16* | (2006.01) |
| *A61B 5/0205* | (2006.01) |
| *A61B 5/024* | (2006.01) |
| *A61B 5/11* | (2006.01) |
| *A61B 5/22* | (2006.01) |
| *G01C 22/00* | (2006.01) |
| *G06F 19/00* | (2011.01) |
| *A61B 5/021* | (2006.01) |

(52) U.S. Cl.
CPC .............. *G06F 1/1694* (2013.01); *G06F 3/011* (2013.01); *G06F 17/21* (2013.01); *G06F 19/3481* (2013.01); *H04L 67/22* (2013.01); *H04W 4/206* (2013.01); *A61B 5/021* (2013.01); *A61B 5/024* (2013.01); *A61B 5/02055* (2013.01); *A61B 5/1112* (2013.01); *A61B 5/222* (2013.01); *A61B 5/4809* (2013.01); *A61B 5/4812* (2013.01); *A61B 5/4815* (2013.01); *A61B 5/6838* (2013.01); *A61B 5/743* (2013.01); *A61B 2560/0214* (2013.01); *A61B 2560/0242* (2013.01); *A61B 2562/0219* (2013.01); *G01C 22/006* (2013.01); *G06F 19/3406* (2013.01)

(56) References Cited

U.S. PATENT DOCUMENTS

| | | |
|---|---|---|
| 2,883,255 A | 4/1959 | Anderson |
| 3,163,856 A | 12/1964 | Kirby |
| 3,250,270 A | 5/1966 | Walter |
| 3,522,383 A | 7/1970 | Chang |
| 3,918,658 A | 11/1975 | Beller |
| 4,192,000 A | 3/1980 | Lipsey |
| 4,244,020 A | 1/1981 | Ratcliff |
| 4,281,663 A | 8/1981 | Pringle |
| 4,284,849 A | 8/1981 | Anderson et al. |
| 4,312,358 A | 1/1982 | Barney |
| 4,367,752 A | 1/1983 | Jimenez et al. |
| 4,390,922 A | 6/1983 | Pelliccia |
| 4,407,295 A | 10/1983 | Steuer et al. |
| 4,425,921 A | 1/1984 | Fujisaki et al. |
| 4,575,804 A | 3/1986 | Ratcliff |
| 4,578,769 A | 3/1986 | Frederick |
| 4,617,525 A | 10/1986 | Lloyd |
| 4,887,249 A | 12/1989 | Thinesen |
| 4,977,509 A | 12/1990 | Pitchford et al. |
| 5,058,427 A | 10/1991 | Brandt |
| 5,224,059 A | 6/1993 | Nitta et al. |
| 5,295,085 A | 3/1994 | Hoffacker |
| 5,323,650 A | 6/1994 | Fullen et al. |
| 5,365,930 A | 11/1994 | Takashima et al. |
| 5,446,705 A | 8/1995 | Haas et al. |
| 5,456,648 A | 10/1995 | Edinburg et al. |
| 5,553,296 A | 9/1996 | Forrest et al. |
| 5,583,776 A | 12/1996 | Levi et al. |
| 5,645,509 A | 7/1997 | Brewer et al. |
| 5,671,162 A | 9/1997 | Werbin |
| 5,704,350 A | 1/1998 | Williams, III |
| 5,724,265 A | 3/1998 | Hutchings |
| 5,890,128 A | 3/1999 | Diaz et al. |
| 5,891,042 A | 4/1999 | Sham et al. |
| 5,894,454 A | 4/1999 | Kondo |
| 5,899,963 A | 5/1999 | Hutchings |
| 5,941,828 A | 8/1999 | Archibald et al. |
| 5,947,868 A | 9/1999 | Dugan |
| 5,955,667 A | 9/1999 | Fyfe |
| 5,976,083 A | 11/1999 | Richardson et al. |
| 6,018,705 A | 1/2000 | Gaudet et al. |
| 6,077,193 A | 6/2000 | Buhler et al. |
| 6,085,248 A | 7/2000 | Sambamurthy et al. |
| 6,129,686 A | 10/2000 | Friedman |
| 6,145,389 A | 11/2000 | Ebeling et al. |
| 6,183,425 B1 | 2/2001 | Whalen et al. |
| 6,213,872 B1 | 4/2001 | Harada et al. |
| 6,241,684 B1 | 6/2001 | Amano et al. |
| 6,287,262 B1 | 9/2001 | Amano et al. |
| 6,301,964 B1 | 10/2001 | Fyfe et al. |
| 6,302,789 B2 | 10/2001 | Harada et al. |
| 6,305,221 B1 | 10/2001 | Hutchings |
| 6,309,360 B1 | 10/2001 | Mault |
| 6,469,639 B2 | 10/2002 | Tanenhaus et al. |
| 6,478,736 B1 | 11/2002 | Mault |
| 6,513,381 B2 | 2/2003 | Fyfe et al. |
| 6,513,532 B2 | 2/2003 | Mault et al. |
| 6,527,711 B1 | 3/2003 | Stivoric et al. |
| 6,529,827 B1 | 3/2003 | Beason et al. |
| 6,558,335 B1 | 5/2003 | Thede |
| 6,561,951 B2 | 5/2003 | Cannon et al. |
| 6,571,200 B1 | 5/2003 | Mault |
| 6,585,622 B1 | 7/2003 | Shum et al. |
| 6,607,493 B2 | 8/2003 | Song |
| 6,620,078 B2 | 9/2003 | Pfeffer |
| 6,678,629 B2 | 1/2004 | Tsuji |
| 6,699,188 B2 | 3/2004 | Wessel |
| 6,761,064 B2 | 7/2004 | Tsuji |
| 6,790,178 B1 | 9/2004 | Mault et al. |
| 6,808,473 B2 | 10/2004 | Hisano et al. |
| 6,811,516 B1 | 11/2004 | Dugan |
| 6,813,582 B2 | 11/2004 | Levi et al. |
| 6,813,931 B2 | 11/2004 | Yadav et al. |
| 6,856,938 B2 | 2/2005 | Kurtz |
| 6,862,575 B1 | 3/2005 | Anttila et al. |
| 7,041,032 B1 | 5/2006 | Calvano |
| 7,062,225 B2 | 6/2006 | White |
| 7,133,690 B2 | 11/2006 | Ranta-Aho et al. |
| 7,162,368 B2 | 1/2007 | Levi et al. |
| 7,171,331 B2 | 1/2007 | Vock et al. |
| 7,200,517 B2 | 4/2007 | Darley et al. |
| 7,246,033 B1 | 7/2007 | Kudo |
| 7,261,690 B2 | 8/2007 | Teller et al. |
| 7,272,982 B2 | 9/2007 | Neuhauser et al. |
| 7,285,090 B2 | 10/2007 | Stivoric et al. |
| 7,373,820 B1 | 5/2008 | James |
| 7,443,292 B2 | 10/2008 | Jensen et al. |
| 7,457,724 B2 | 11/2008 | Vock et al. |
| 7,467,060 B2 | 12/2008 | Kulach et al. |
| 7,502,643 B2 | 3/2009 | Farringdon et al. |
| 7,505,865 B2 | 3/2009 | Ohkubo et al. |
| 7,539,532 B2 | 5/2009 | Tran |
| 7,558,622 B2 | 7/2009 | Tran |
| 7,559,877 B2 | 7/2009 | Parks et al. |
| 7,653,508 B1 | 1/2010 | Kahn et al. |
| 7,690,556 B1 | 4/2010 | Kahn et al. |
| 7,713,173 B2 | 5/2010 | Shin et al. |

(56) References Cited

U.S. PATENT DOCUMENTS

| | | |
|---|---|---|
| 7,762,952 B2 | 7/2010 | Lee et al. |
| 7,771,320 B2 | 8/2010 | Riley et al. |
| 7,774,156 B2 | 8/2010 | Niva et al. |
| 7,789,802 B2 | 9/2010 | Lee et al. |
| 7,881,902 B1 | 2/2011 | Kahn et al. |
| 7,927,253 B2 | 4/2011 | Vincent et al. |
| 7,983,876 B2 | 7/2011 | Vock et al. |
| 8,028,443 B2 | 10/2011 | Case, Jr. |
| 8,055,469 B2 | 11/2011 | Kulach et al. |
| 8,099,318 B2 | 1/2012 | Moukas et al. |
| 8,132,037 B2 | 3/2012 | Fehr et al. |
| 8,177,260 B2 | 5/2012 | Tropper et al. |
| 8,180,591 B2 | 5/2012 | Yuen et al. |
| 8,180,592 B2 | 5/2012 | Yuen et al. |
| 8,270,297 B2 | 9/2012 | Akasaka et al. |
| 8,311,769 B2 | 11/2012 | Yuen et al. |
| 8,311,770 B2 | 11/2012 | Yuen et al. |
| 8,386,008 B2 | 2/2013 | Yuen et al. |
| 8,437,980 B2 | 5/2013 | Yuen et al. |
| 8,462,591 B1 | 6/2013 | Marhaben |
| 8,463,576 B2 | 6/2013 | Yuen et al. |
| 8,463,577 B2 | 6/2013 | Yuen et al. |
| 8,533,620 B2 | 9/2013 | Hoffman et al. |
| 8,543,185 B2 | 9/2013 | Yuen et al. |
| 8,543,351 B2 | 9/2013 | Yuen et al. |
| 8,548,770 B2 | 10/2013 | Yuen et al. |
| 8,562,489 B2 | 10/2013 | Burton et al. |
| 8,583,402 B2 | 11/2013 | Yuen et al. |
| 8,597,093 B2 | 12/2013 | Engelberg et al. |
| 8,634,796 B2 | 1/2014 | Johnson |
| 8,670,953 B2 | 3/2014 | Yuen et al. |
| 8,690,578 B1 | 4/2014 | Nusbaum et al. |
| 8,738,321 B2 | 5/2014 | Yuen et al. |
| 8,738,323 B2 | 5/2014 | Yuen et al. |
| 8,744,803 B2 | 6/2014 | Park et al. |
| 8,762,101 B2 | 6/2014 | Yuen et al. |
| 8,764,651 B2 | 7/2014 | Tran |
| 8,847,988 B2 | 9/2014 | Geisner et al. |
| 8,954,290 B2 * | 2/2015 | Yuen ............... G06F 3/011 702/160 |
| 8,968,195 B2 | 3/2015 | Tran |
| 2001/0049470 A1 | 12/2001 | Mault et al. |
| 2001/0055242 A1 | 12/2001 | Deshmukh et al. |
| 2002/0013717 A1 | 1/2002 | Ando et al. |
| 2002/0019585 A1 | 2/2002 | Dickenson |
| 2002/0077219 A1 | 6/2002 | Cohen et al. |
| 2002/0082144 A1 | 6/2002 | Pfeffer |
| 2002/0087264 A1 | 7/2002 | Hills et al. |
| 2002/0109600 A1 | 8/2002 | Mault et al. |
| 2002/0178060 A1 | 11/2002 | Sheehan |
| 2002/0198776 A1 | 12/2002 | Nara et al. |
| 2003/0018523 A1 | 1/2003 | Rappaport et al. |
| 2003/0050537 A1 | 3/2003 | Wessel |
| 2003/0065561 A1 | 4/2003 | Brown et al. |
| 2003/0131059 A1 | 7/2003 | Brown et al. |
| 2004/0054497 A1 | 3/2004 | Kurtz |
| 2004/0061324 A1 | 4/2004 | Howard |
| 2004/0117963 A1 | 6/2004 | Schneider |
| 2004/0152957 A1 | 8/2004 | Stivoric et al. |
| 2004/0239497 A1 | 12/2004 | Schwartzman et al. |
| 2004/0249299 A1 | 12/2004 | Cobb |
| 2005/0037844 A1 | 2/2005 | Shum et al. |
| 2005/0038679 A1 | 2/2005 | Short |
| 2005/0054938 A1 | 3/2005 | Wehman et al. |
| 2005/0102172 A1 | 5/2005 | Sirmans, Jr. |
| 2005/0107723 A1 | 5/2005 | Wehman et al. |
| 2005/0163056 A1 | 7/2005 | Ranta-Aho et al. |
| 2005/0171410 A1 | 8/2005 | Hjelt et al. |
| 2005/0228244 A1 | 10/2005 | Banet |
| 2005/0228692 A1 | 10/2005 | Hodgdon |
| 2005/0234742 A1 | 10/2005 | Hodgdon |
| 2005/0248718 A1 | 11/2005 | Howell et al. |
| 2005/0272564 A1 | 12/2005 | Pyles et al. |
| 2006/0020174 A1 | 1/2006 | Matsumura |
| 2006/0020177 A1 | 1/2006 | Seo et al. |
| 2006/0025282 A1 | 2/2006 | Redmann |
| 2006/0047208 A1 | 3/2006 | Yoon |
| 2006/0047447 A1 | 3/2006 | Brady et al. |
| 2006/0064276 A1 * | 3/2006 | Ren et al. .................. 702/160 |
| 2006/0069619 A1 | 3/2006 | Walker et al. |
| 2006/0089542 A1 | 4/2006 | Sands |
| 2006/0111944 A1 | 5/2006 | Sirmans, Jr. |
| 2006/0129436 A1 | 6/2006 | Short |
| 2006/0143645 A1 | 6/2006 | Vock et al. |
| 2006/0217231 A1 | 9/2006 | Parks et al. |
| 2006/0247952 A1 | 11/2006 | Muraca |
| 2006/0277474 A1 | 12/2006 | Robarts et al. |
| 2006/0282021 A1 | 12/2006 | DeVaul et al. |
| 2006/0287883 A1 | 12/2006 | Turgiss et al. |
| 2007/0050715 A1 | 3/2007 | Behar |
| 2007/0051369 A1 | 3/2007 | Choi et al. |
| 2007/0071643 A1 | 3/2007 | Hall et al. |
| 2007/0072156 A1 | 3/2007 | Kaufman et al. |
| 2007/0083602 A1 | 4/2007 | Heggenhougen et al. |
| 2007/0123391 A1 | 5/2007 | Shin et al. |
| 2007/0136093 A1 | 6/2007 | Rankin et al. |
| 2007/0146116 A1 | 6/2007 | Kimbrell |
| 2007/0155277 A1 | 7/2007 | Amitai et al. |
| 2007/0159926 A1 | 7/2007 | Prstojevich et al. |
| 2007/0179356 A1 | 8/2007 | Wessel |
| 2007/0194066 A1 | 8/2007 | Ishihara et al. |
| 2007/0197920 A1 | 8/2007 | Adams |
| 2007/0208544 A1 | 9/2007 | Kulach et al. |
| 2007/0276271 A1 | 11/2007 | Chan |
| 2007/0288265 A1 | 12/2007 | Quinian et al. |
| 2008/0001735 A1 | 1/2008 | Tran |
| 2008/0022089 A1 | 1/2008 | Leedom |
| 2008/0032864 A1 | 2/2008 | Hakki |
| 2008/0084823 A1 | 4/2008 | Akasaka et al. |
| 2008/0093838 A1 | 4/2008 | Tropper et al. |
| 2008/0097550 A1 | 4/2008 | Dicks et al. |
| 2008/0114829 A1 * | 5/2008 | Button et al. .................. 709/203 |
| 2008/0125288 A1 | 5/2008 | Case |
| 2008/0129457 A1 | 6/2008 | Ritter et al. |
| 2008/0134102 A1 * | 6/2008 | Movold et al. ................ 715/863 |
| 2008/0140163 A1 | 6/2008 | Keacher et al. |
| 2008/0140338 A1 | 6/2008 | No et al. |
| 2008/0146892 A1 | 6/2008 | LeBoeuf et al. |
| 2008/0155077 A1 | 6/2008 | James |
| 2008/0176655 A1 | 7/2008 | James et al. |
| 2009/0018797 A1 | 1/2009 | Kasama et al. |
| 2009/0043531 A1 | 2/2009 | Kahn et al. |
| 2009/0047645 A1 | 2/2009 | Dibenedetto et al. |
| 2009/0048044 A1 | 2/2009 | Oleson et al. |
| 2009/0054737 A1 | 2/2009 | Magar et al. |
| 2009/0063193 A1 | 3/2009 | Barton et al. |
| 2009/0098821 A1 | 4/2009 | Shinya |
| 2009/0150178 A1 | 6/2009 | Sutton et al. |
| 2009/0156172 A1 * | 6/2009 | Chan ......................... 455/412.2 |
| 2009/0171788 A1 | 7/2009 | Tropper et al. |
| 2009/0195350 A1 | 8/2009 | Tsern et al. |
| 2009/0262088 A1 | 10/2009 | Moll-Carrillo et al. |
| 2009/0264713 A1 | 10/2009 | Van Loenen et al. |
| 2009/0271147 A1 | 10/2009 | Sugai |
| 2009/0287921 A1 | 11/2009 | Zhu et al. |
| 2009/0307517 A1 | 12/2009 | Fehr et al. |
| 2009/0309742 A1 * | 12/2009 | Alexander et al. ............. 340/601 |
| 2010/0059561 A1 | 3/2010 | Ellis et al. |
| 2010/0069203 A1 | 3/2010 | Kawaguchi et al. |
| 2010/0159709 A1 | 6/2010 | Kotani et al. |
| 2010/0167783 A1 * | 7/2010 | Alameh et al. ............. 455/556.1 |
| 2010/0185064 A1 | 7/2010 | Bandic et al. |
| 2010/0205541 A1 | 8/2010 | Rapaport et al. |
| 2010/0217099 A1 | 8/2010 | LeBoeuf et al. |
| 2010/0331145 A1 | 12/2010 | Lakovic et al. |
| 2011/0003665 A1 | 1/2011 | Burton et al. |
| 2011/0009051 A1 | 1/2011 | Khedouri et al. |
| 2011/0022349 A1 | 1/2011 | Stirling et al. |
| 2011/0080349 A1 | 4/2011 | Holbein et al. |
| 2011/0087076 A1 | 4/2011 | Brynelsen et al. |
| 2011/0106449 A1 | 5/2011 | Chowdhary et al. |
| 2011/0131005 A1 | 6/2011 | Ueshima et al. |
| 2011/0193704 A1 | 8/2011 | Harper et al. |
| 2011/0197157 A1 | 8/2011 | Hoffman et al. |

(56) References Cited

U.S. PATENT DOCUMENTS

| | | |
|---|---|---|
| 2011/0224508 A1 | 9/2011 | Moon |
| 2011/0230729 A1 | 9/2011 | Shirasaki et al. |
| 2012/0072165 A1 | 3/2012 | Jallon |
| 2012/0083705 A1 | 4/2012 | Yuen et al. |
| 2012/0083714 A1 | 4/2012 | Yuen et al. |
| 2012/0083715 A1 | 4/2012 | Yuen et al. |
| 2012/0083716 A1 | 4/2012 | Yuen et al. |
| 2012/0084053 A1 | 4/2012 | Yuen et al. |
| 2012/0084054 A1 | 4/2012 | Yuen et al. |
| 2012/0092157 A1 | 4/2012 | Tran |
| 2012/0094649 A1 | 4/2012 | Porrati et al. |
| 2012/0119911 A1 | 5/2012 | Jeon et al. |
| 2012/0165684 A1 | 6/2012 | Sholder |
| 2012/0183939 A1 | 7/2012 | Aragones et al. |
| 2012/0226471 A1 | 9/2012 | Yuen et al. |
| 2012/0226472 A1 | 9/2012 | Yuen et al. |
| 2012/0227737 A1 | 9/2012 | Mastrototaro et al. |
| 2012/0265480 A1 | 10/2012 | Oshima |
| 2012/0274508 A1 | 11/2012 | Brown et al. |
| 2012/0290109 A1* | 11/2012 | Engelberg ........... G06F 19/3481 700/91 |
| 2012/0316456 A1 | 12/2012 | Rahman et al. |
| 2012/0324226 A1 | 12/2012 | Bichsel et al. |
| 2012/0330109 A1 | 12/2012 | Tran |
| 2013/0006718 A1 | 1/2013 | Nielsen et al. |
| 2013/0041590 A1 | 2/2013 | Burich et al. |
| 2013/0072169 A1 | 3/2013 | Ross et al. |
| 2013/0073254 A1 | 3/2013 | Yuen et al. |
| 2013/0073255 A1 | 3/2013 | Yuen et al. |
| 2013/0080113 A1 | 3/2013 | Yuen et al. |
| 2013/0095459 A1 | 4/2013 | Tran |
| 2013/0096843 A1 | 4/2013 | Yuen et al. |
| 2013/0106684 A1 | 5/2013 | Weast et al. |
| 2013/0151196 A1 | 6/2013 | Yuen et al. |
| 2013/0158369 A1 | 6/2013 | Yuen et al. |
| 2013/0166048 A1 | 6/2013 | Werner et al. |
| 2013/0190903 A1 | 7/2013 | Balakrishnan et al. |
| 2013/0191034 A1 | 7/2013 | Weast et al. |
| 2013/0228063 A1 | 9/2013 | Turner |
| 2013/0231574 A1 | 9/2013 | Tran |
| 2013/0238287 A1 | 9/2013 | Hoffman et al. |
| 2013/0261475 A1 | 10/2013 | Mochizuki |
| 2013/0267249 A1 | 10/2013 | Rosenberg |
| 2013/0268199 A1 | 10/2013 | Nielsen et al. |
| 2013/0268236 A1 | 10/2013 | Yuen et al. |
| 2013/0268687 A1 | 10/2013 | Schrecker |
| 2013/0274904 A1 | 10/2013 | Coza et al. |
| 2013/0289366 A1 | 10/2013 | Chua et al. |
| 2013/0296666 A1 | 11/2013 | Kumar et al. |
| 2013/0296672 A1 | 11/2013 | O'Neil et al. |
| 2013/0296673 A1 | 11/2013 | Thaveeprungsriporn et al. |
| 2013/0310896 A1 | 11/2013 | Mass |
| 2013/0325396 A1 | 12/2013 | Yuen et al. |
| 2013/0337974 A1 | 12/2013 | Yanev et al. |
| 2014/0035761 A1 | 2/2014 | Burton et al. |
| 2014/0039804 A1 | 2/2014 | Park et al. |
| 2014/0039840 A1 | 2/2014 | Yuen et al. |
| 2014/0039841 A1 | 2/2014 | Yuen et al. |
| 2014/0052280 A1 | 2/2014 | Yuen et al. |
| 2014/0067278 A1 | 3/2014 | Yuen et al. |
| 2014/0077673 A1 | 3/2014 | Garg et al. |
| 2014/0094941 A1 | 4/2014 | Ellis et al. |
| 2014/0125618 A1 | 5/2014 | Panther et al. |
| 2014/0164611 A1 | 6/2014 | Molettiere et al. |
| 2014/0213858 A1 | 7/2014 | Presura et al. |
| 2014/0275885 A1 | 9/2014 | Isaacson et al. |
| 2014/0278229 A1 | 9/2014 | Hong et al. |
| 2014/0316305 A1 | 10/2014 | Venkatraman et al. |

FOREIGN PATENT DOCUMENTS

| | | |
|---|---|---|
| WO | 0211019 A1 | 2/2002 |
| WO | 2006055125 A1 | 5/2006 |
| WO | 2006090197 A1 | 8/2006 |
| WO | 2008038141 A2 | 4/2008 |
| WO | 2009042965 A1 | 4/2009 |

OTHER PUBLICATIONS

Activity Classification Using Realistic Data From Wearable Sensors, Parkka, et al., IEEE Transactions on Information Technology in Biomedicine, vol. 10, No. 1, Jan. 2006, pp. 119-128.

Altimeter and Barometer System, Clifford, et al., Freescale Semiconductor Aplication Note AN1979, Rev. 3, Nov. 2006.

An Intelligent Multi-Sensor system for Pedestrian Navigation, Retscher, Journal of Global Positioning Systems, vol. 5, No. 1, 2006, pp. 110-118.

Automatic classification of ambulatory movements and evaluation of energy consumptions utilizing accelerometers and barometer, Ohtaki, et al, Microsystem Technologies, vol. 11, No. 8-10, Aug. 2005, pp. 1034-1040.

Classification of Human Moving Patterns Using Air Pressure and Acceleration, Sagawa, et al., Proceedings of the 24th Annual Conference of the IEEE Industrial Electronics Society, vol. 2, Aug.-Sep. 1998, pp. 1214-1219.

Deepak et al., Plug-and-Play, Single-Chip Photoplethysmography, 34th Annual International Conference of the IEEE EMBS, San Diego, California USA, Aug. 28-Sep. 1, 2012, 4 pages.

Design of a Wireless Assisted Pedestrian Dead Reckoning System—The NavMote Experience, Fang, et al., IEEE Transactions on Instrumentation and Measurement, vol. 54, No. 6, Dec. 2005, pp. 2342-2358.

Direct Measurement of Human Movement by Accelerometry, Godfrey, et al., Medical Engineering & Physics, vol. 30, 2008, pp. 1364-1386.

Drift-free dynamic height sensor using MEMS IMU aided by MEMS pressure sensor, Tanigawa, et al., Workshop on Positioning, Navigation and Communication, Mar. 2008, pp. 191-196.

Evaluation of a New Method of Heading Estimation of Pedestrian Dead Reckoning Using Shoe Mounted Sensors, Stirling et al., Journal of Navigation, vol. 58, 2005, pp. 31-45.

Foot Mounted Inertial System for Pedestrian Navigation, Godha et al., Measurement Science and Technology, vol. 19, No. 7, May 2008, pp. 1-9.

Improvement of Walking Speed Prediction by Accelerometry and Altimetry, Validated by Satellite Positioning, Perrin, et al., Medical & Biological Engineering & Computing, vol. 38, 2000, pp. 164-168.

Indoor Navigation with MEMS Sensors, Lammel, et al., Proceedings of the Eurosensors XIII conference, vol. 1, No. 1, Sep. 2009, pp. 532-535.

International Search Report issued on Aug. 15, 2008, in related application PCT/IB07/03617.

Non-restricted measurement of walking distance, Sagawa, et al., IEEE Int'l Conf. on Systems, Man, and Cybernetics, vol. 3, Oct. 2000, pp. 1847-1852.

On Foot Navigation: When GPS alone is not Enough, Ladetto, et al., Journal of Navigation, vol. 53, No. 2, Sep. 2000, pp. 279-285.

SCP 1000-D01/D11 Pressure Sensor as Barometer and Altimeter, VTI Technologies Application, Jun. 2006, Note 33.

Specification of the Bluetooth® System, Core Package, version 4.1, Dec. 2013, vols. 0 & 1, 282 pages.

Suunto LUMI User Guide, Jun. and Sep. 1997.

Using MS5534 for altimeters and barometers, Intersema App., Note AN501, Jan. 2006.

Validated caloric expenditure estimation using a single body-worn sensor, Lester, et al., Proc. of the Int'l Conf. on Ubiquitous Computing, 2009, pp. 225-234.

* cited by examiner

MOTION-ACTIVATED DISPLAY OF MESSAGES ON AN ACTIVITY MONITORING DEVICE

CLAIM OF PRIORITY

This application is a continuation of U.S. patent application Ser. No. 14/271,389, filed on May 6, 2014, titled "Motion-Activated Display of Messages on an Activity Monitoring Device, which is a continuation-in-part of U.S. patent application Ser. No. 13/959,714, published as U.S. Patent Application Publication No. 20140039841, filed on Aug. 5, 2013, titled "Methods and Systems for Identification of Event Data Having Combined Activity and Location Information of Portable Monitoring Devices," which is a continuation-in-part of U.S. patent application Ser. No. 13/693,334, now U.S. Pat. No. 8,548,770, filed on Dec. 4, 2012, titled "Portable Monitoring Devices and Methods for Operating Same", which is a divisional of U.S. patent application Ser. No. 13/667,229, now U.S. Pat. No. 8,437,980, filed on Nov. 2, 2012, titled "Portable Monitoring Devices and Methods for Operating Same", which is a divisional of U.S. patent application Ser. No. 13/469,027, now U.S. Pat. No. 8,311,769, filed on May 10, 2012, titled "Portable Monitoring Devices and Methods for Operating Same", which is a divisional of U.S. patent application Ser. No. 13/246,843, now U.S. Pat. No. 8,180,591, filed on Sep. 27, 2011, which is a divisional of U.S. patent application Ser. No. 13/156,304, published as U.S. Patent Application Publication No. 20120083715, filed on Jun. 8, 2011, titled "Portable Monitoring Devices and Methods for Operating Same", which claims the benefit of and priority to, under 35 U.S.C. 119§(e), to U.S. Provisional Patent Application No. 61/388,595, filed on Sep. 30, 2010, and titled "Portable Monitoring Devices and Methods for Operating Same", and to U.S. Provisional Patent Application No. 61/390,811, filed on Oct. 7, 2010, and titled "Portable Monitoring Devices and Methods for Operating Same", all of which are hereby incorporated by reference in their entirety.

U.S. patent application Ser. No. 13/959,714 is a continuation-in-part of U.S. patent application Ser. No. 13/759,485, now U.S. Pat. No. 8,543,351, filed on Feb. 5, 2013, titled "Portable Monitoring Devices and Methods for Operating Same", which is a divisional of U.S. patent application Ser. No. 13/667,229, filed on Nov. 2, 2012, titled "Portable Monitoring Devices and Methods for Operating Same", which is a divisional of U.S. patent application Ser. No. 13/469,027, now U.S. Pat. No. 8,311,769, filed on May 10, 2012, titled "Portable Monitoring Devices and Methods for Operating Same", which is a divisional of U.S. patent application Ser. No. 13/246,843, now U.S. Pat. No. 8,180,591, filed on Sep. 27, 2011, which is a divisional of U.S. patent application Ser. No. 13/156,304, filed on Jun. 8, 2011, titled "Portable Monitoring Devices and Methods for Operating Same", which claims the benefit of and priority to, under 35 U.S.C. 119§(e), to U.S. Provisional Patent Application No. 61/388,595, filed on Sep. 30, 2010, and titled "Portable Monitoring Devices and Methods for Operating Same" and to U.S. Provisional Patent Application No. 61/390,811, filed on Oct. 7, 2010, and titled "Portable Monitoring Devices and Methods for Operating Same", all of which are hereby incorporated by reference in their entirety.

FIELD

The present disclosure relates to systems and methods for motion-activated display of messages on an activity monitoring device.

BACKGROUND

In recent years, the need for health and fitness has grown tremendously. The growth has occurred due to a better understanding of the benefits of good fitness to overall health and wellness. Unfortunately, although today's modern culture has brought about many new technologies, such as the Internet, connected devices and computers, people have become less active. Additionally, many office jobs require people to sit in front of computer screens for long periods of time, which further reduces a person's activity levels. Furthermore, much of today's entertainment options involve viewing multimedia content, computer social networking, and other types of computer involved interfacing. Although such computer activity can be very productive as well as entertaining, such activity tends to reduce a person's overall physical activity.

To provide users concerned with health and fitness a way of measuring or accounting for their activity or lack thereof, fitness activity trackers have recently grown in popularity. Fitness activity trackers are used to measure activity, such as walking, motion, running, sleeping, being inactive, bicycling, exercising on an elliptical trainer, and the like. Typically, the data collected by such devices can be transferred and viewed on a computing device. However, while fitness activity trackers enable many data-intensive features relating to fitness activity, interfacing with a fitness activity tracker can feel sterile and robotic to a user.

It is in this context that embodiments of the invention arise.

SUMMARY

Embodiments described in the present disclosure provide systems, apparatus, computer readable media, and methods for displaying motion-activated messages on a portable activity monitoring device.

In one embodiment, a method for presenting a message on an activity monitoring device is provided, including: storing a plurality of messages to the device; detecting a non-user interactive state of the device; detecting a change of the device from the non-user interactive state to a user-interactive state; in response to detecting the change from the non-user interactive state to the user-interactive state, selecting one of a plurality of messages, and displaying the selected message on the device; wherein selecting one of the plurality of messages is based on one or more of a length of time of the non-user interactive state, a current time of day, a current location of the device, or an activity history associated with a user of the device; wherein the method is executed by at least one processor.

In one embodiment, detecting the non-user interactive state includes detecting a stationary state that is defined by non-movement of the device for a predefined time period; and detecting the change of the device from the non-user interactive state to the user-interactive state includes detecting a movement of the device from the stationary state.

In one embodiment, detecting the change from the non-user interactive state to the user interactive state includes detecting a movement of the device from a first orientation to a second orientation.

In one embodiment, detecting the non-user interactive state includes detecting a charging state of the device; and detecting the change from the non-user interactive state to the user interactive state includes detecting a change of the device from the charging state to a non-charging state.

In one embodiment, detecting the change from the non-user interactive state to the user interactive state includes detecting one or more of a button press or a touchscreen input.

In one embodiment, the device is configured to detect one or more of the following activities by a user: steps taken, energy consumed, elevation gained, active minutes.

In one embodiment, storing the plurality of messages includes identifying the device to a server and downloading the plurality of messages from the server, the server being configured to access a user account associated with the device, the plurality of messages being selected by the server based on the user account.

In one embodiment, at least one of the plurality of messages is defined based on one or more of a current date, a location of the device, a current season, or a current weather.

In one embodiment, at least one of the plurality of messages is defined based on an activity history of a user associated with the device.

In one embodiment, the activity history is defined by levels of activity associated to specific time periods.

In one embodiment, at least one of the plurality of messages is defined by input received from a secondary user, the secondary user being a member of a social graph of a primary user associated with the device.

In one embodiment, the operations of selecting and displaying are not performed during a time period for which an event is scheduled in a calendar of a user of the device.

In another embodiment, a method for presenting a message on an activity monitoring device is provided, comprising: storing a plurality of messages to the device; detecting a stationary state of the device; detecting a movement of the device from the stationary state; in response to detecting the movement from the stationary state, selecting one of a plurality of messages, and displaying the selected message on the device; wherein at least one of the plurality of messages is defined based on one or more of a current date, a location of the device, a current season, or a current weather; wherein the method is executed by at least one processor.

In one embodiment, detecting the stationary state includes detecting non-movement of the device for a predefined time period.

In one embodiment, storing the plurality of messages includes identifying the device to a server and downloading the plurality of messages from the server, the server being configured to access a user account associated with the device, the plurality of messages being selected by the server based on the user account.

In one embodiment, at least one of the plurality of messages is defined based on an activity history of a user associated with the device.

In one embodiment, the activity history is defined by levels of activity associated to specific time periods.

In one embodiment, at least one of the plurality of messages is defined by input received from a secondary user, the secondary user being a member of a social graph of a primary user associated with the device.

In one embodiment, the operations of selecting and displaying are not performed during a time period for which an event is scheduled in a calendar of a user of the device.

In another embodiment, an activity monitoring device is provided, comprising: a message storage device configured to store a plurality of messages; a motion sensor; a display; logic configured to detect, based on output of the motion sensor, a stationary state of the device and a subsequent movement of the device from the stationary state, and, in response to detecting the movement from the stationary state, select one of the plurality of messages, and display the selected message on the device; wherein at least one of the plurality of messages is defined based on an activity history of a user associated with the device; wherein the method is executed by at least one processor.

In one embodiment, detecting the stationary state includes detecting non-movement of the device for a predefined time period.

In one embodiment, selecting one of the plurality of messages is based on one or more of a length of time of the stationary state, a current time of day, a current location of the device, or an activity history associated with a user of the device.

In one embodiment, at least one of the plurality of messages is defined based on one or more of a current date, a location of the device, a current season, or a current weather.

In one embodiment, the activity history is defined by levels of activity associated to specific time periods.

In one embodiment, at least one of the plurality of messages is defined by input received from a secondary user, the secondary user being a member of a social graph of a primary user associated with the device.

In one embodiment, the activity monitoring device further comprises: logic configured to download the plurality of messages to the message storage, wherein the downloading includes identifying the device to a server, the server being configured to access a user account associated with the device, the plurality of messages being selected by the server based on the user account.

In another embodiment, an activity monitoring device is provided, comprising: a message storage device configured to store a plurality of messages; a motion sensor; a display; logic configured to detect, based on output of the motion sensor, a stationary state of the device and a subsequent movement of the device from the stationary state, and, in response to detecting the movement from the stationary state, select one of the plurality of messages, and display the selected message on the device; wherein at least one of the plurality of messages is defined by input received from a secondary user, the secondary user being a member of a social graph of a primary user associated with the device; wherein the method is executed by at least one processor.

In one embodiment, detecting the stationary state includes detecting non-movement of the device for a predefined time period.

In one embodiment, selecting one of the plurality of messages is based on one or more of a length of time of the stationary state, a current time of day, a current location of the device, or an activity history associated with a user of the device.

In one embodiment, at least one of the plurality of messages is defined based on one or more of a current date, a location of the device, a current season, or a current weather.

In one embodiment, at least one of the plurality of messages is defined based on an activity history of a user associated with the device.

In one embodiment, the activity history is defined by levels of activity associated to specific time periods.

In one embodiment, the activity monitoring device further comprises: logic configured to download the plurality of messages to the message storage, wherein the downloading includes identifying the device to a server, the server being configured to access a user account associated with the device, the plurality of messages being selected by the server based on the user account.

In another embodiment, a method for presenting a message on an activity monitoring device is provided, comprising: storing a plurality of messages to the device; detecting a stationary state of the device; detecting a movement of the device from the stationary state; in response to detecting the movement from the stationary state, selecting one of a plurality of messages, and displaying the selected message on the device; wherein the operations of selecting and displaying are not performed during a time period for which an event is scheduled in a calendar of a user of the device; wherein the method is executed by at least one processor.

In another embodiment, a method for presenting messages on an activity monitoring device is provided, including the following method operations: receiving a request to synchronize the device with a user account to which the device is associated; retrieving profile data from the user account; selecting one or more messages from a message storage based on the profile data; sending the selected messages to the device, the device configured to display at least one of the selected messages in response to detecting movement of the device from a stationary state.

In one embodiment, the profile data defines one or more of an age, a gender, a location, or a historical activity profile.

In one embodiment, selecting one or more messages is based on one or more of a current date, a current day of the week, a current location of the device, an activity history associated with a user of the device, a current season, a current weather, and social network activity.

In one embodiment, one of the selected messages is defined by a secondary user, the secondary user being a member of a social graph of a primary user associated with the device.

Other aspects will become apparent from the following detailed description, taken in conjunction with the accompanying drawings, illustrating by way of example the principles of embodiments described in the present disclosure.

BRIEF DESCRIPTION OF THE DRAWINGS

Various embodiments described in the present disclosure may best be understood by reference to the following description taken in conjunction with the accompanying drawings.

DETAILED DESCRIPTION

Figure 1A:
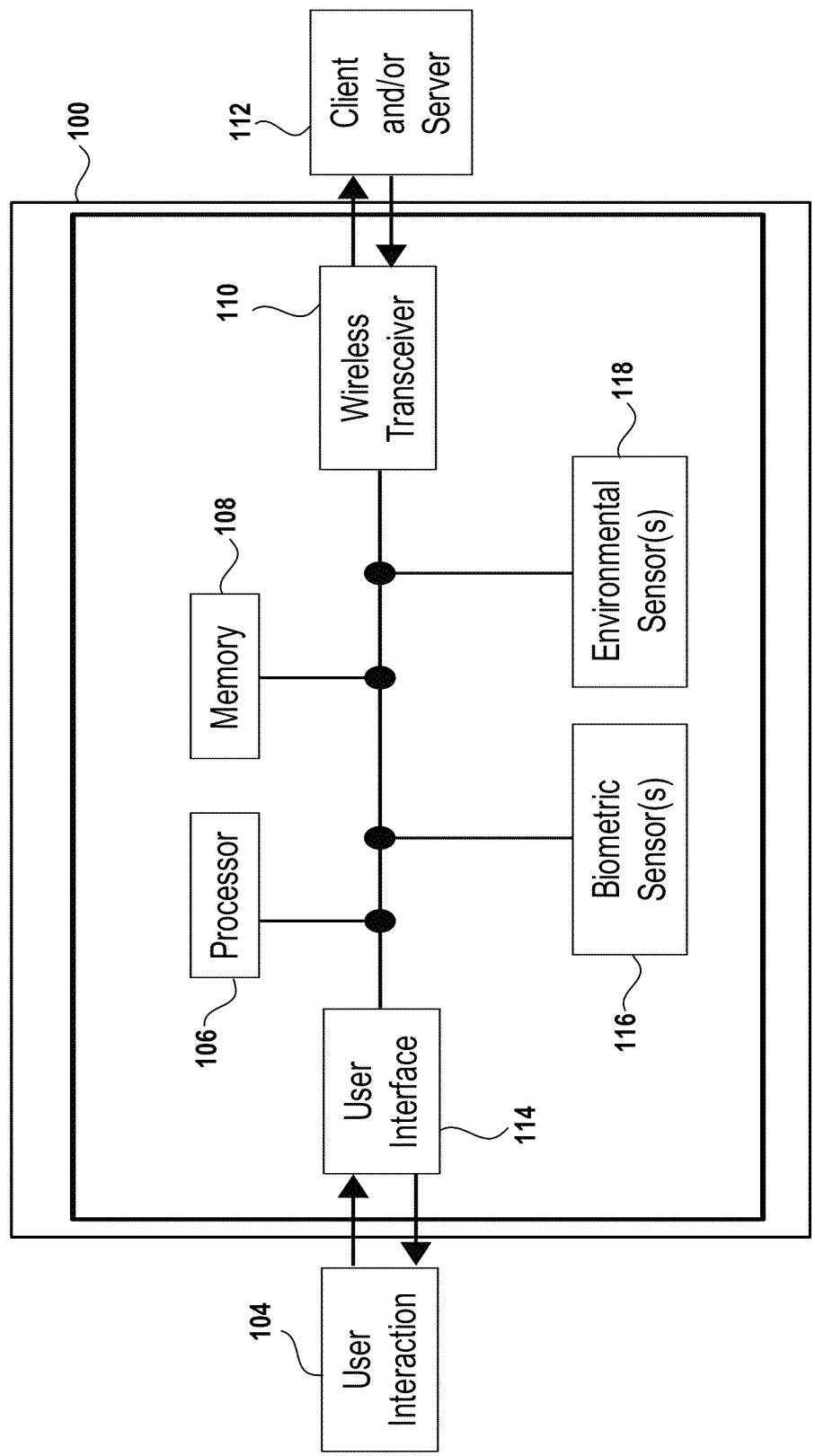
FIG. 1A shows a block diagram of an activity tracking device, in accordance with one embodiment of the present invention.

Embodiments described in the present disclosure provide systems, apparatus, computer readable media, and methods for displaying motion-activated messages on a portable activity monitoring device.

It should be noted that there are many inventions described and illustrated herein. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

Further, in the course of describing and illustrating the present inventions, various circuitry, architectures, structures, components, functions and/or elements, as well as combinations and/or permutations thereof, are set forth. It should be understood that circuitry, architectures, structures, components, functions and/or elements other than those specifically described and illustrated, are contemplated and are within the scope of the present inventions, as well as combinations and/or permutations thereof.

FIG. 1 shows a block diagram of an activity tracking device 100, in accordance with one embodiment of the present invention. The activity tracking device 100 is contained in a housing, which may be worn or held by a user. The housing may be in the form of a wristband, a clip on device, a wearable device, or may be held by the user either in the user's hand or in a pocket or attached to the user's body. The activity tracking device 100 includes device components 102, which may be in the form of logic, storage, and glue logic, one or more processors, microelectronics, and interfacing circuitry. In one example, the components 102 will include a processor 106, memory 108, a wireless transceiver 110, a user interface 114, biometric sensors 116, and environmental sensors 118.

The environmental sensors 118 may be in the form of motion detecting sensors. In some embodiments, a motion sensor can be one or more of an accelerometer, or a gyroscope, or a rotary encoder, or a calorie measurement sensor, or a heat measurement sensor, or a moisture measurement sensor, or a displacement sensor, or an ultrasonic sensor, or a pedometer, or an altimeter, or a linear motion sensor, or an angular motion sensor, or a multi-axis motion sensor, or a combination thereof. The biometric sensors 116 can be defined to measure physiological characteristics of the user that is using the activity tracking device 100. The user interface 114 provides a way for communicating with the activity tracking device 100, in response to user interaction 104. The user interaction 104 can be in the form of physical contact (e.g., without limitation, tapping, sliding, rubbing, multiple taps, gestures, etc.).

In some embodiments, the user interface 114 is configured to receive user interaction 104 by way of proximity sensors, button presses, touch sensitive screen inputs, graphical user interface inputs, voice inputs, sound inputs, etc. The activity tracking device 100 can communicate with a client and/or server 112 using the wireless transceiver 110. The wireless transceiver 110 will allow the activity tracking device 100 to communicate using a wireless connection, which is enabled by wireless communication logic. The wireless communication logic can be in the form of a circuit having radio communication capabilities. The radio communication capabilities can be in the form of a Wi-Fi connection, a Bluetooth connection, a low-energy Bluetooth connection, or any other form of wireless tethering or near field communication. In still other embodiments, the activity tracking device 100 can communicate with other computing devices using a wired connection (not shown). As mentioned, the environmental sensors 118 can detect motion of the activity tracking device 100.

The motion can be activity of the user, such as walking, running, stair climbing, etc. The motion can also be in the form of physical contact received on any surface of the activity tracking device 110, so long as the environmental sensors 118 can detect such motion from the physical contact. Such physical contact may be in the form of a tap or multiple taps by a finger upon the housing of the activity tracking device 100.

Figure 1B:
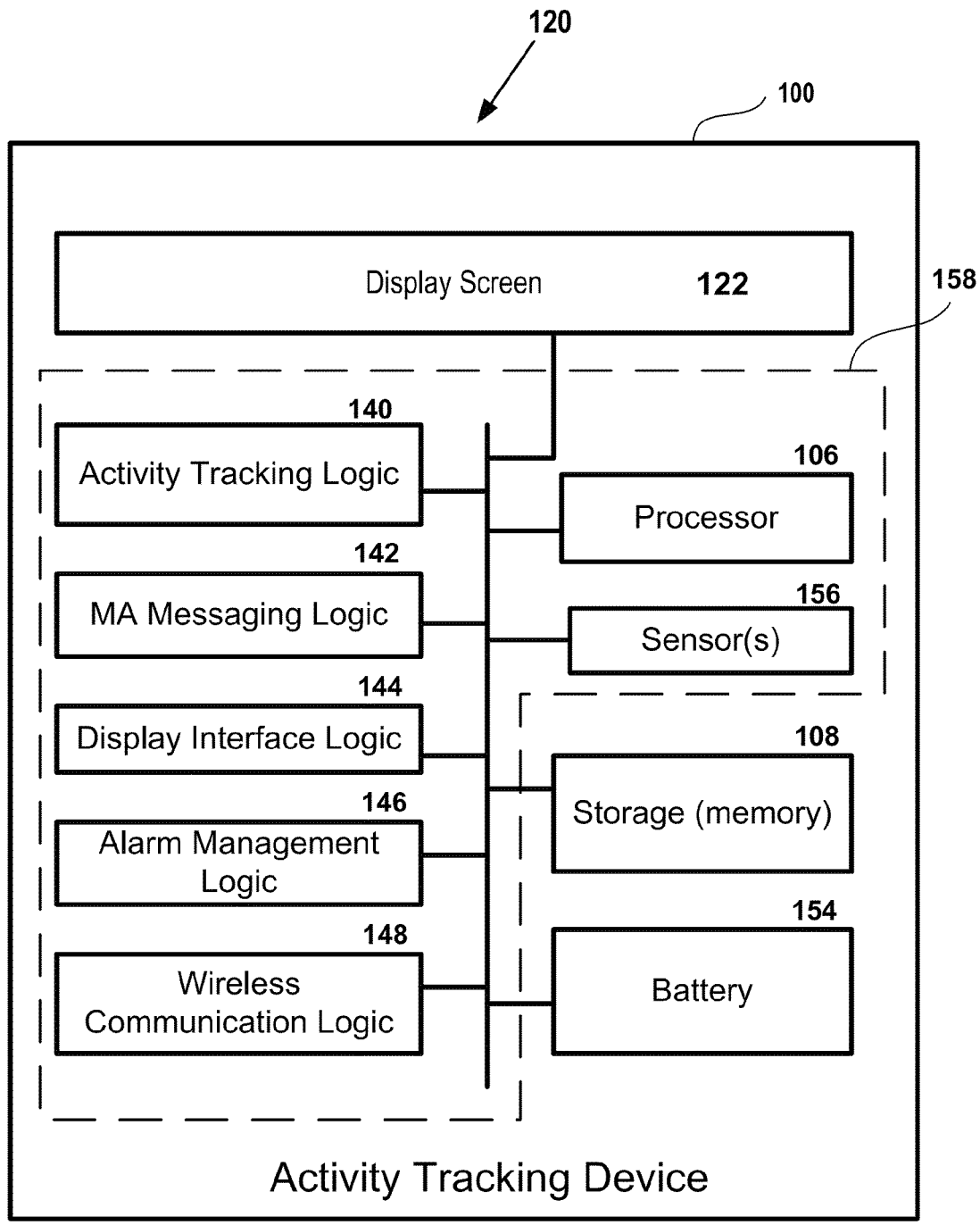
FIG. 1B illustrates an example of an activity tracking device including example components utilized for tracking activity and motion of the device, and associated interfaces to a display screen, in accordance with one embodiment of the present invention.

FIG. 1B illustrates an example of activity tracking device 100 of FIG. 1A, showing some additional example components utilized for tracking activity and motion of the device, and associated interfaces to display screen 122. In one embodiment, examples of a display screen 122 can include, but are not limited to, liquid crystal display (LCD) screens, light emitting diode (LED) screens, organic light emitting diode (OLED) screens, plasma display screens, etc.

As shown in FIG. 1B, the activity tracking device 100 includes logic 158. Logic 158 may include activity tracking logic 140, motion-activated messaging logic 142, display interface logic 144, alarm management logic 146, wireless communication logic 148, processor 106, and sensors 156. Additionally, storage (e.g. memory) 108, and a battery 154 can be integrated within the activity tracking device 100. The activity tracking logic 140 can include logic that is configured to process motion data produced by sensors 156, so as to quantify the motion and produce identifiable metrics associated with the motion.

Some motions will produce and quantify various types of metrics, such as step count, stairs climbed, distance traveled, very active minutes, calories burned, etc. The physical contact logic 142 can include logic that calculates or determines when particular physical contact can qualify as an input. To qualify as an input, the physical contact detected by sensors 156 should have a particular pattern that is identifiable as input. For example, the input may be predefined to be a double tap input, and the physical contact logic 142 can analyze the motion to determine if a double tap indeed occurred in response to analyzing the sensor data produced by sensors 156.

The display interface logic 144 is configured to interface with the processor and the motion-activated messaging logic to determine when specific messages will be displayed on the display screen 122 of the activity tracking device 100. The display interface logic 144 can act to turn on the screen, display metric information, display characters or alphanumeric information, display graphical user interface graphics, or combinations thereof. Alarm management logic 146 can function to provide a user interface and settings for managing and receiving input from a user to set an alarm. The alarm management logic can interface with a timekeeping module (e.g., clock, calendar, time zone, etc.), and can trigger the activation of an alarm. The alarm can be in the form of an audible alarm or a non-audible alarm.

A non-audible alarm can provide such alarm by way of a vibration. The vibration can be produced by a motor integrated in the activity tracking device 100. The vibration can be defined to include various vibration patterns, intensities, and custom set patterns. The vibration produced by the motor or motors of the activity tracking device 100 can be managed by the alarm management logic 146 in conjunction with processing by the processor 106. The wireless communication logic 148 is configured for communication of the activity tracking device with another computing device by way of a wireless signal. The wireless signal can be in the form of a radio signal. As noted above, the radio signal can be in the form of a Wi-Fi signal, a Bluetooth signal, a low energy Bluetooth signal, or combinations thereof. The wireless communication logic can interface with the processor 106, storage 108 and battery 154 of device 100, for transferring activity data, which may be in the form of motion data or processed motion data, stored in the storage 108 to the computing device.

In one embodiment, processor 106 functions in conjunction with the various logic components 140, 142, 144, 146, and 148. The processor 106 can, in one embodiment, provide the functionality of any one or all of the logic components. In other embodiments, multiple chips can be used to separate the processing performed by any one of the logic components and the processor 106. Sensors 156 can communicate via a bus with the processor 106 and/or the logic components. The storage 108 is also in communication with the bus for providing storage of the motion data processed or tracked by the activity tracking device 100. Battery 154 is provided for providing power to the activity tracking device 100.

Figure 2:
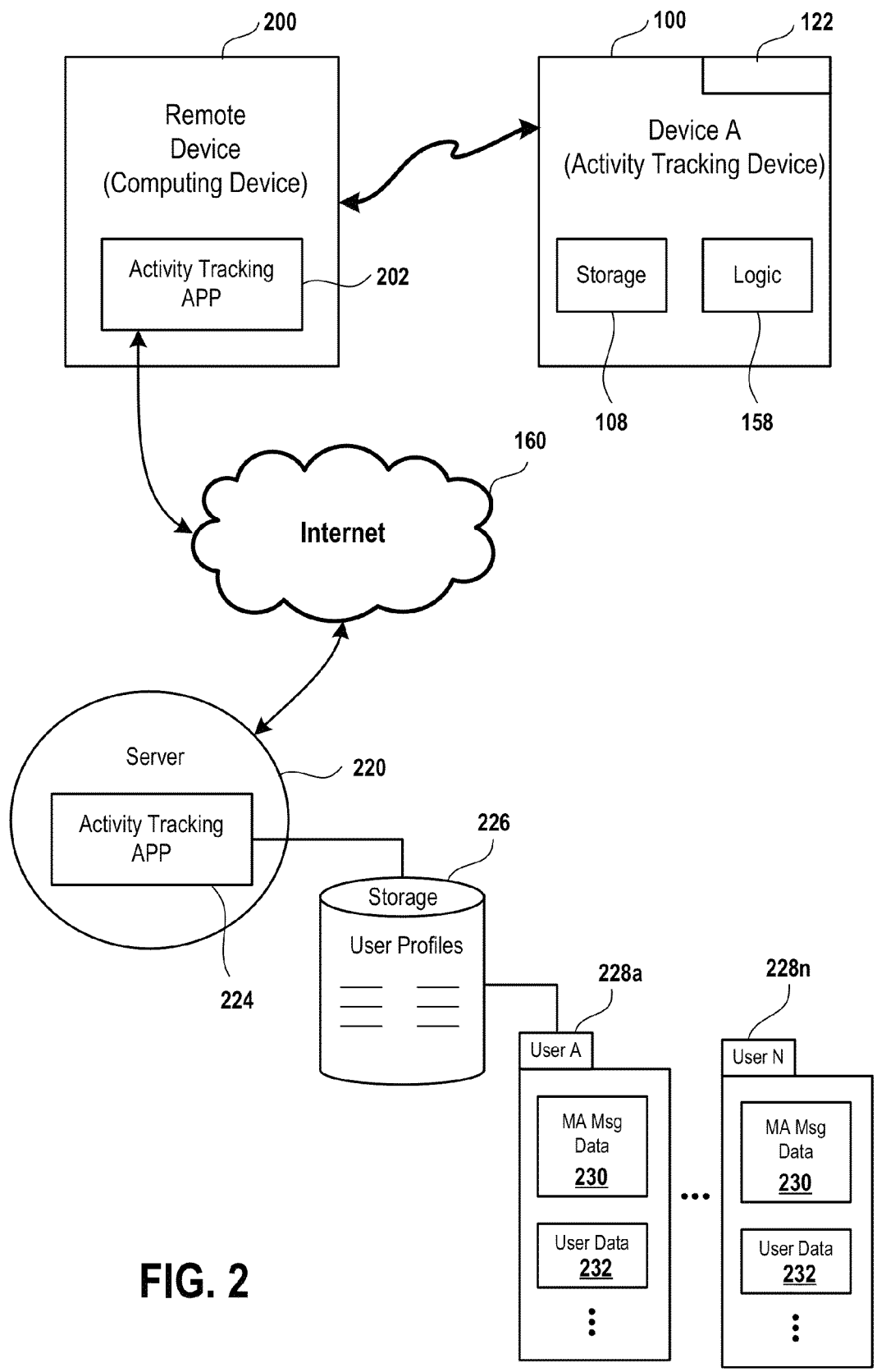
FIG. 2 illustrates an example of activity tracking device in communication with a remote device, in accordance with one embodiment of the present invention.

FIG. 2 illustrates an example of activity tracking device 100 in communication with a remote device 200. Remote device 200 is a computing device that is capable of communicating wirelessly with activity tracking device 100 and with the Internet 160. Remote device 200 can support installation and execution of applications. Such applications can include an activity tracking application 202. Activity tracking application 202 can be downloaded from a server. The server can be a specialized server or a server that provides applications to devices, such as an application store. Once the activity tracking application 202 is installed in the remote device 200, the remote device 200 can communicate or be set to communicate with activity tracking device 100 (Device A). The remote device 200 can be a smartphone, a handheld computer, a tablet computer, a laptop computer, a desktop computer, or any other computing device capable of wirelessly interfacing with Device A and the Internet.

In one embodiment, remote device 200 communicates with activity tracking device 100 over a Bluetooth connection. In one embodiment, the Bluetooth connection is a low energy Bluetooth connection (e.g., Bluetooth LE, BLE, or Bluetooth Smart). Low energy Bluetooth is configured for providing low power consumption relative to standard Bluetooth circuitry. Low energy Bluetooth uses, in one embodiment, a 2.4 GHz radio frequency, which allows for dual mode devices to share a single radio antenna. In one embodiment, low energy Bluetooth connections can function at distances up to 50 meters, with over the air data rates ranging between 1-3 megabits (Mb) per second. In one embodiment, a proximity distance for communication can be defined by the particular wireless link, and is not tied to any specific standard. It should be understood that the proximity distance limitation will change in accordance with changes to existing standards and in view of future standards and/or circuitry and capabilities.

Remote device 200 can also communicate with the Internet 160 using an Internet connection. The Internet connection of the remote device 200 can include cellular connections, wireless connections such as Wi-Fi, and combinations thereof (such as connections to switches between different types of connection links). The remote device, as mentioned above, can be a smartphone or tablet computer, or any other type of computing device having access to the Internet and with capabilities for communicating with the activity tracking device 100.

A server 220 is also provided, which is interfaced with the Internet 160. The server 220 can include a number of applications that service the activity tracking device 100, and the associated users of the activity tracking device 100 by way of user accounts. For example, the server 220 can include an activity management application 224. The activity management application 224 can include logic for providing access to various devices 100, which are associated with user accounts managed by server 220. Server 220 can include storage 226 that includes various user profiles associated with the various user accounts. The user account 228a for user A and the user account 228n for user N are shown to include various information.

The information can include, without limitation, data associated with motion-activated messaging 230, user data, etc. As will be described in greater detail below, the motion-activated messaging data 230 includes information regarding a user's preferences, settings, and configurations which are settable by the user or set by default at the server 220 when accessing a respective user account. The storage 226 will include any number of user profiles, depending on the number of registered users having user accounts for their respective activity tracking devices. It should also be noted that a single user account can have various or multiple devices associated therewith, and the multiple devices can be individually customized, managed and accessed by a user. In one embodiment, the server 220 provides access to a user to view the user data 232 associated with activity tracking device.

The data viewable by the user includes the tracked motion data, which is processed to identify a plurality of metrics associated with the motion data. The metrics are shown in various graphical user interfaces of a website enabled by the server 220. The website can include various pages with graphical user interfaces for rendering and displaying the various metrics for view by the user associated with the user account. In one embodiment, the website can also include interfaces that allow for data entry and configuration by the user.

Figure 3A:
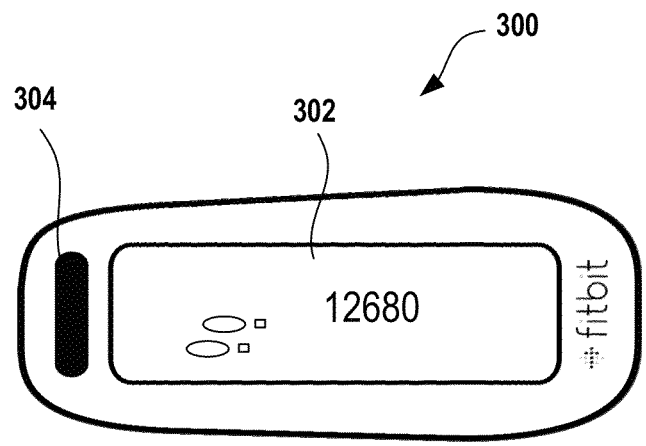
FIG. 3A illustrates a perspective view of a portable activity monitoring device, in accordance with an embodiment of the invention.

FIG. 3A illustrates a perspective view of a portable activity monitoring device, in accordance with an embodiment of the invention. The activity monitoring device 300 is shown to include a display 302 for displaying various data such as text or images. In one embodiment, the display 302 can be configured to display video. In the illustrated embodiment, the display 302 is currently displaying a step count, indicating the number of steps taken that have been detected by the activity monitoring device 300 over some defined time period (e.g. the current day or week). The activity monitoring device 300 is also shown to include a button 304. In one embodiment, the button 304 may be pressed to cycle the display of various fitness statistics which have been stored on the device 300. By way of example, these may include a number of steps taken, a number of floors climbed, distance traveled, a number of active minutes, a number of calories burned, an activity amount remaining in order to reach a particular goal, etc. Additionally, the button 304 may be pressed to turn on/off the display 302.

In some embodiments, additional information that may be of use to a user may be accessed by pressing the button 304, such as a current date or time, a battery charge level, a date/time of the device's last data sync (i.e. transfer of data from the activity monitoring device 300 to an external device), a pairing mode for pairing the activity monitoring device to an external device, an option to reset a fitness activity counter, an option to turn the device off, etc. Additionally, it should be appreciated that the button may be pressed in various ways to facilitate access to various features. By way of example, the button may be pressed once, pressed and held, pressed twice in rapid succession, etc. For example, pressing and holding the button 304 may turn the device 300 on or off.

Figure 3B:
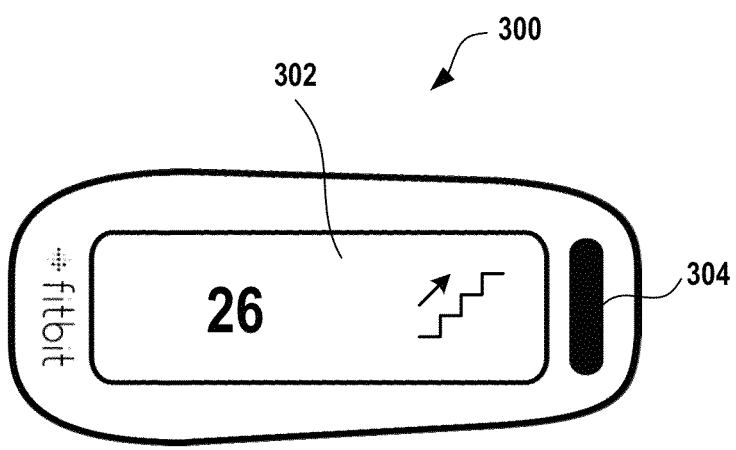
FIG. 3B illustrates a top view of an activity monitoring device, in accordance with an embodiment of the invention.

FIG. 3B illustrates a top view of the activity monitoring device 300, in accordance with an embodiment of the invention. In the illustrated embodiment, a number of floors climbed is currently displayed on the display 302 of the activity monitoring device 300.

Figure 3C:
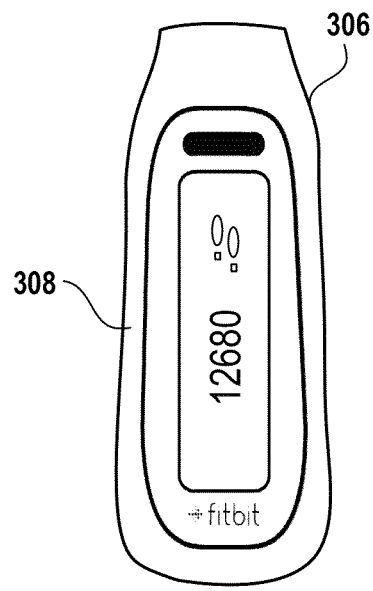
FIG. 3C illustrates a top view of an activity monitoring device disposed in a carrying case, in accordance with an embodiment of the invention.

FIG. 3C illustrates a top view of the activity monitoring device 300 disposed in a carrying case 306, in accordance with an embodiment of the invention. The carrying case 306 defines a sheath 308 which extends around the sides and back of the activity monitoring device 300 so as to secure it in the carrying case 306, while leaving exposed the top surface of the activity monitoring device 300.

Figure 3D:
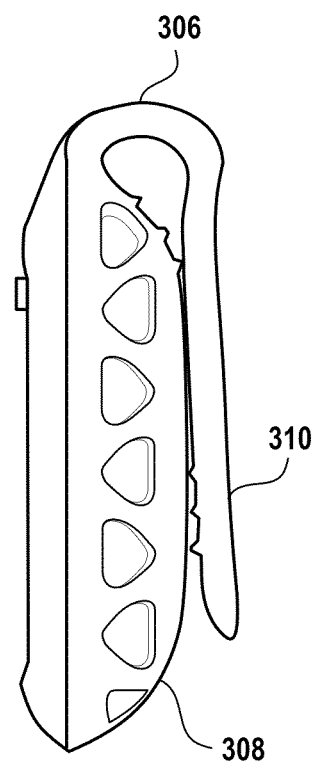
FIG. 3D illustrates a side view of an activity monitoring device disposed in a carrying case, in accordance with an embodiment of the invention.

FIG. 3D illustrates a side view of the activity monitoring device 300 disposed in carrying case 306. As can be seen, the carrying case 306 includes an extension 310 which extends adjacent to the sheath 308, thus allowing the carrying case 306 to function as a clip, so that the device 300 and carrying case 306 can be attached to a user (e.g. attached to the user's clothing).

Figure 4:
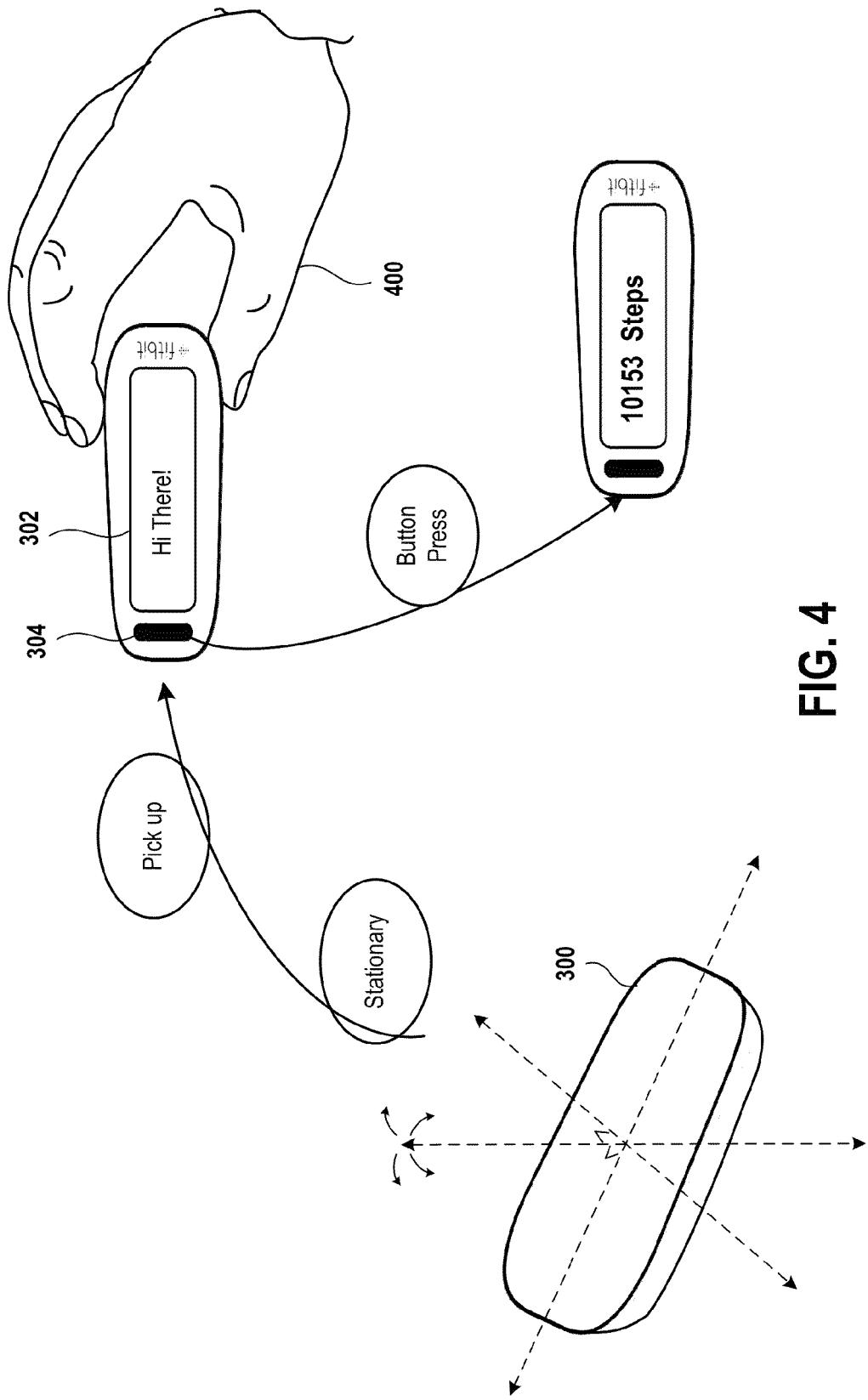
FIG. 4 conceptually illustrates the display of a motion-activated message on a portable activity monitoring device, in accordance with an embodiment of the invention.

FIG. 4 conceptually illustrates the display of a motion-activated message on a portable activity monitoring device, in accordance with an embodiment of the invention. In one embodiment, a message can be displayed on the display 302 of the activity monitoring device 300 in response to detection of a movement of the device 300 from a stationary position.

The stationary position can be defined to require the device to be maintained in a non-moving or stationary state for a predefined length of time. For example, in one embodiment, the stationary position requires the device to be not moving for approximately two to three seconds. In other embodiments, the stationary position is defined to require the device to be not moving for any specified length of time.

Furthermore, it will be appreciated that the stationary state may be defined by the absence of movements exceeding a predefined threshold for a specified length of time. It should be appreciated that the specific types of movements and the predefined threshold can be defined in various ways. For example, in one embodiment, the movement is defined by the sensor output of motion-sensitive hardware included in the activity monitoring device, such as accelerometers, gravitometers, gyroscopes, etc., and the predefined threshold may be defined by a specific magnitude of a given sensor output (e.g. detected acceleration of the device exceeds an acceleration threshold). It will be appreciated that a combination of sensor outputs and corresponding thresholds can be considered. In one embodiment, a weighted combination (e.g., a weighted sum) of motion sensor outputs is defined and compared against a predefined threshold. In this manner, certain types of movements may be prioritized over others for purposes of identifying movement from a stationary state. For example, in one embodiment, translational movement of the device is prioritized over rotational movement, such that sensor outputs which are indicative of translational movement are more highly weighted than sensor outputs which are indicative of rotational movement.

In other embodiments, the detected movement and corresponding predefined threshold can be defined based on particular types of movements which are determined or derived from motion sensor output. For example, in one embodiment, a distance moved is determined for the device, and the device is defined to be in a stationary state so long as the distance moved by the device does not exceed a predefined distance threshold. In one embodiment, the detection of the distance moved is reset following a period of zero movement. In another embodiment, the detection of the distance moved is cumulative. By defining the stationary state based on the absence of movement exceeding a predefined threshold, false positive movements can be avoided, so that motion-activated messages are not displayed when the movements are of low significance or unlikely to be the result of intentional movement of the device warranting display of a motion-activated message.

Additionally, the stationary position can be defined to require not only a lack of movement of the activity monitoring device 300, but also a specific orientation of the activity monitoring device 300 in three-dimensional space. For example, in one embodiment, the device 300 is required to be in a substantially horizontal orientation, that is, the orientation that the device 300 has when it is laying on a substantially horizontal flat surface, with the top side of the device 300 (the side on which the display 302 may be viewed by a user) facing upward.

Thus, in accordance with the foregoing, a motion-activated message can be displayed when the following events are detected: non-movement of the device; orientation of the activity monitoring device in a specified orientation; maintenance of the non-movement and specified orientation for a minimum specified length of time; and, following the maintenance of the non-movement and specified orientation, movement of the activity monitoring device (e.g. translational and/or rotational movement). The completion of the preceding events can be configured to trigger presentation of a motion-activated message on the display 302 of the activity monitoring device 300.

As shown with continued reference to FIG. 4, the activity monitoring device 300 is detected to be in a stationary position for at least a predefined length of time, following which the device 300 is picked up by a hand 400 of a user. The detection of this movement of the device 300 triggers the presentation of a motion-activated message ("Hi there!") on the display 302. Upon pressing the button 304 of the activity monitoring device 300, the motion-activated message ceases to be displayed; and in one embodiment, a fitness activity statistic, such as the user's step count, is presented on the display 302.

Figure 5A:
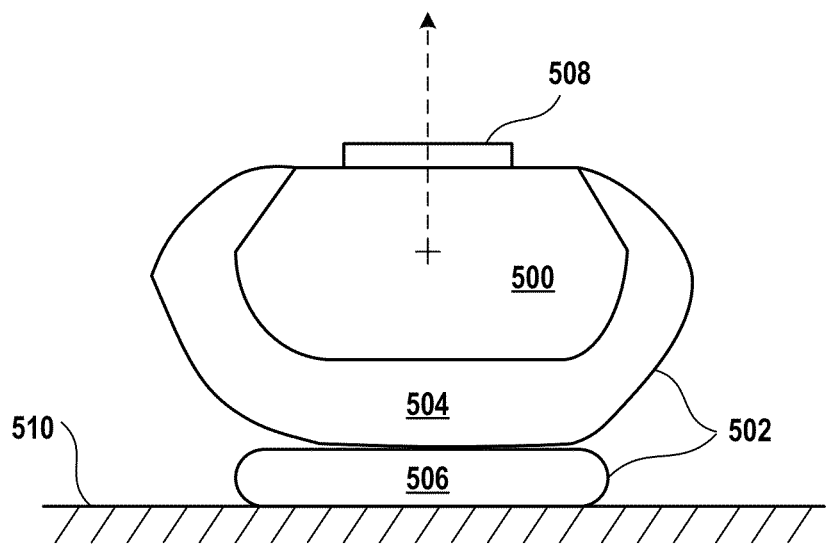
FIG. 5A illustrates a cross-section view of a portable activity monitoring device, in accordance with an embodiment of the invention.

FIG. 5A illustrates a cross-section view of a portable activity monitoring device, in accordance with an embodiment of the invention. As shown, the activity monitoring device 500 is held in a case 502, which includes a sheath portion 504 for securing the device 500 and a clip extension 506 that abuts the sheath portion 504 to enable the case 502 to be clipped to an object, such as an article of clothing. The activity monitoring device and case may be similar to or the same as that described with reference to FIGS. 3A, 3B, 3C, and 3D. The activity monitoring device 500 includes a button 508, which is disposed on the top surface of the device 500. In the illustrated embodiment, the case 502 is shown resting on a substantially horizontal planar surface 510 in an orientation wherein the outward-facing side of the clip extension 506 faces downward and touches the surface 510. As such, the activity monitoring device 500 is therefore oriented with its top surface facing upward.

It should be appreciated that the orientation of the device 500 may be substantially horizontal, or may have a specific tilt depending upon the specific configuration of the case 502, which determines how the device 500 will be oriented when the case 502 is resting on the surface 510 as shown. For example, assuming that the activity monitoring device 500 has a shape that is elongated in a (lengthwise) direction that is substantially orthogonal to the cross-sectional plane shown in FIG. 5A, then the activity monitoring device 500 may be substantially horizontal along its lengthwise direction, or may have a specific lengthwise tilt, when the case is situated on the surface 510 as shown.

It will be appreciated that the configuration of the case 502 in combination with its particular orientation on the surface 510 will determine the orientation of the activity monitoring device 500. In one embodiment, the specific orientation of the activity monitoring device 500 when positioned as shown in FIG. 5A can be detected. That is, the device 500 can be configured to detect when it is positioned so as to have such an orientation, and upon maintenance of the orientation for some predefined time period, the device 500 can be configured to trigger display of a message when the device 500 is moved again.

Figure 5B:
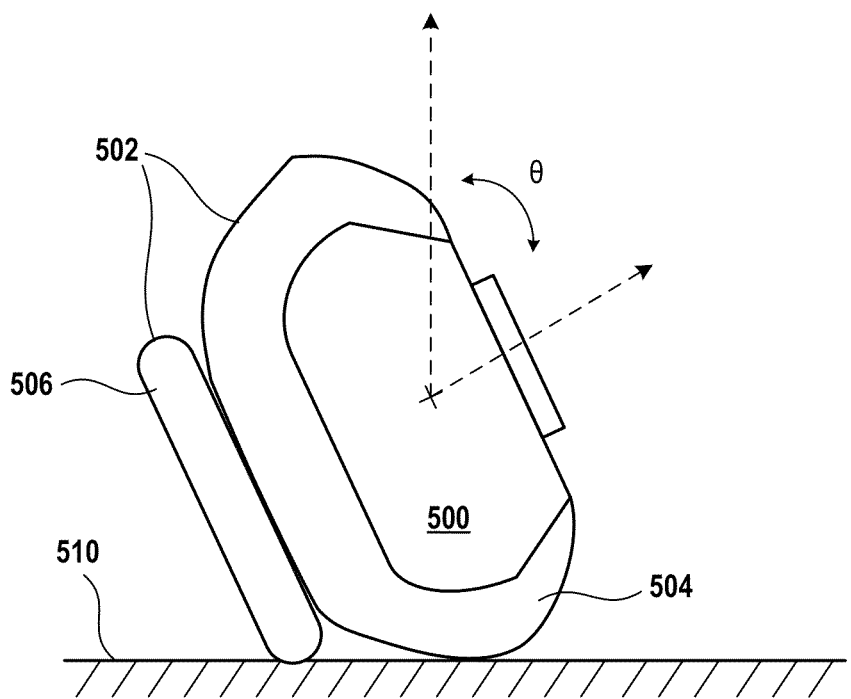
FIG. 5B illustrates a cross-section view of a portable activity monitoring device, in accordance with an embodiment of the invention.

FIG. 5B illustrates a cross-section view of a portable activity monitoring device, in accordance with an embodiment of the invention. In the illustrated embodiment, the case 502 is shown resting on its side on the surface 510, such that side portions of the sheath 504 and extension clip 506 contact the surface 510. In this configuration as shown, the activity monitoring device 500 is also tilted on its (lengthwise) side by an angle θ measured relative to a direction substantially orthogonal to the top surface of the device 500. This tilted configuration of the device 500 resulting from the configuration of the case 502 represents a stable orientation of the case 502 and device 500. That is, it is possible for a user to place the case 502 and device 500 on a substantially horizontal surface in a tilted orientation that will be stable over time.

As such, the orientation of the device in the illustrated embodiment can be detected. When the orientation is detected for a minimum predefined time, subsequent movement of the device from such an orientation can be configured to trigger presentation of a motion-activated message on the display of the device 500.

Figure 5C:
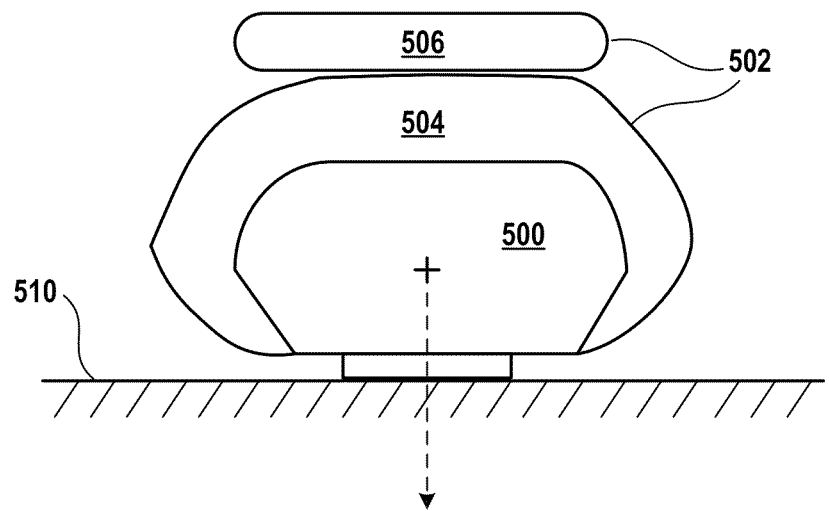
FIG. 5C illustrates an activity monitoring device placed upside-down on a substantially horizontal surface, in accordance with an embodiment of the invention.

FIG. 5C illustrates the activity monitoring device 500 placed upside-down on the substantially horizontal surface 510. In this orientation, the top surface of the activity monitoring device faces downward towards the surface 510. This orientation of the device 500 is another stable orientation, and can be detected by the device 500. As has been discussed, when the orientation is detected as being maintained for a predefined amount of time, subsequent movement of the device 500 from the detected orientation can be configured to trigger display of a message on the display of the device 500.

Figure 6:
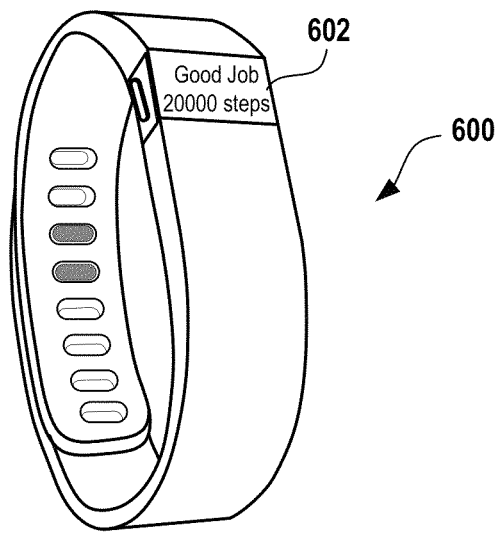
FIG. 6 illustrates an activity monitoring device in the form of a wearable wrist attachable device, in accordance with an embodiment of the invention.

Though reference has been made to an activity monitoring device having a generally elongated shape, it should be appreciated that this form factor for an activity monitoring device is provided by way of example, and not by way of limitation. For example, FIG. 6 illustrates an activity monitoring device in the form of a wearable wrist attachable device, in accordance with an embodiment of the invention. The activity monitoring device 600 includes a display 602 for displaying various kinds of information, including motion-activated messages in accordance with various embodiments described herein.

In one embodiment, the device 600 can be configured to display a motion-activated message on the display 602 when the device 600 is moved from a stable stationary position in which the device 600 lays on its side on a substantially horizontal surface. In the stationary position, an outer edge of the band of the wrist attachable device 600 will contact the surface on which the device 600 rests, and the display 602 will have a sideways orientation. It will be appreciated that the device 600 has two such possible stable stationary positions, one in which the device rests on a right side of the display, and another in which the device rests on the left side of the display. Movement from these stable stationary positions may trigger presentation of a motion-activated message on the display 602.

In other embodiments, a recognizable motion can be detected and may be configured to trigger display of a motion-activated message. For example, with continued reference to the activity monitoring device 600, a detected movement of the device 600 indicating that a user wearing the device has raised their arm so as to view the display 602 may be configured to trigger display of a motion-activated message. Such a motion of the device 600 may be that resulting from simultaneous lifting and pronation of the user's forearm, by way of example. It should be appreciated that a similar concept can be extended to other types of motions and other form factors for the activity monitoring device, wherein an identifiable motion of the activity monitoring device triggers display of a motion-activated message.

Figure 7:
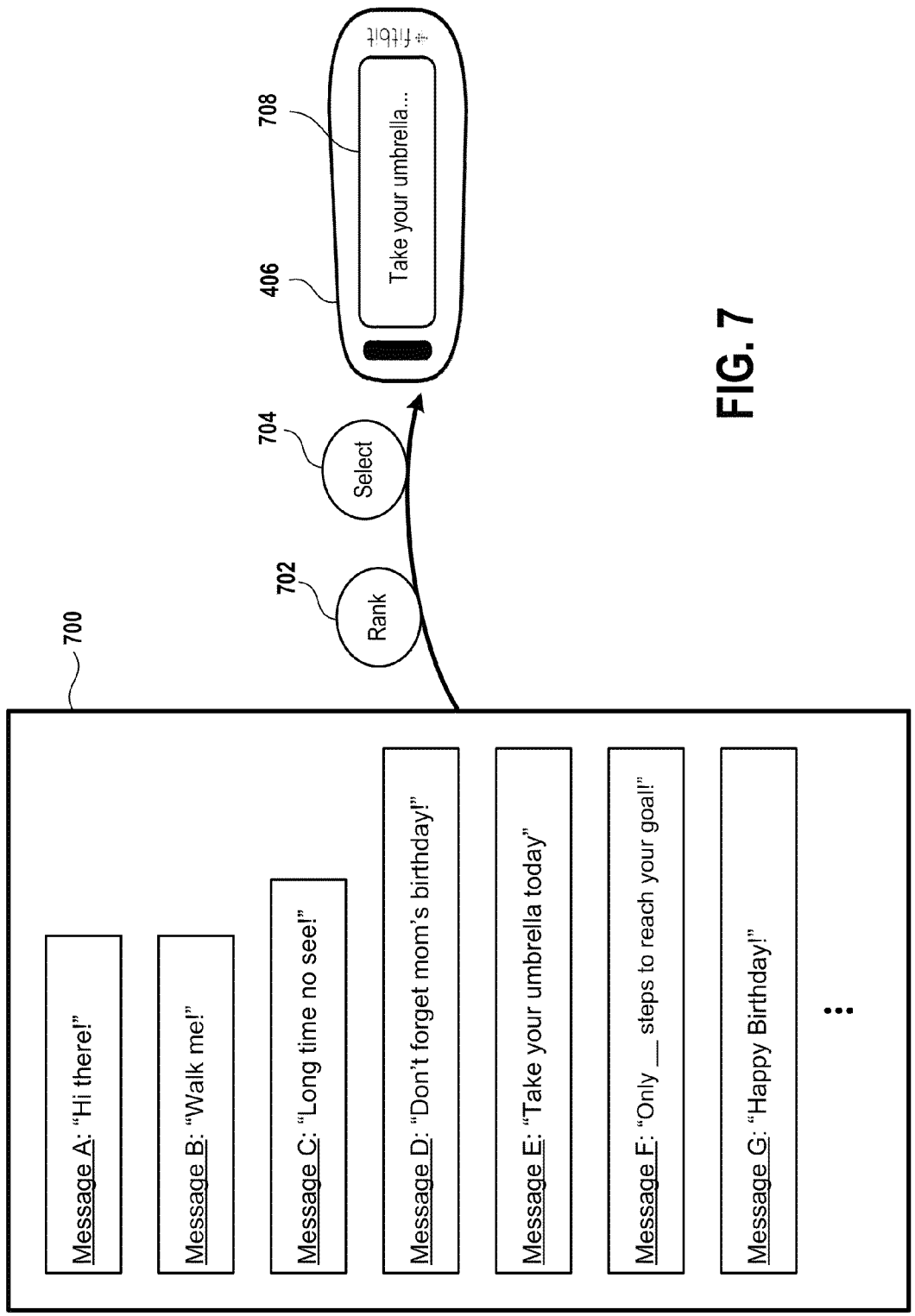
FIG. 7 conceptually illustrates a process for displaying a motion-activated message on an activity monitoring device, in accordance with an embodiment of the invention.

FIG. 7 conceptually illustrates a process for displaying a motion-activated message on an activity monitoring device, in accordance with an embodiment of the invention. In one embodiment, a plurality of motion-activated messages 700 are stored on the activity monitoring device 706. In the illustrated embodiment, the messages 700 include various Messages A, B, C, etc. Each message defines a portion of text for display on the display 708 of the activity monitoring device 706. By way of example, Message A is defined by the text "Hi there!"; Message B is defined by the text "Walk me"; etc.

To determine which one of the messages 700 to display, the messages 700 may be ranked (ref. 702) based on various factors, including without limitation, time/date, prior display, activity/inactivity of the user as detected by the device 706, etc. Additional exemplary factors which may be utilized to rank, or otherwise determine selection from, a plurality of messages, are discussed in further detail below. As indicated at ref. 704, one of the messages is selected for display, based at least in part on the determined ranking. The selected message is displayed on the display 708 of the activity monitoring device 706. It will be appreciated that the presentation of the selected message may be scrolled across the display 708 if the length of the selected message is too long to permit the entirety of the selected message to be displayed simultaneously.

Figure 8:
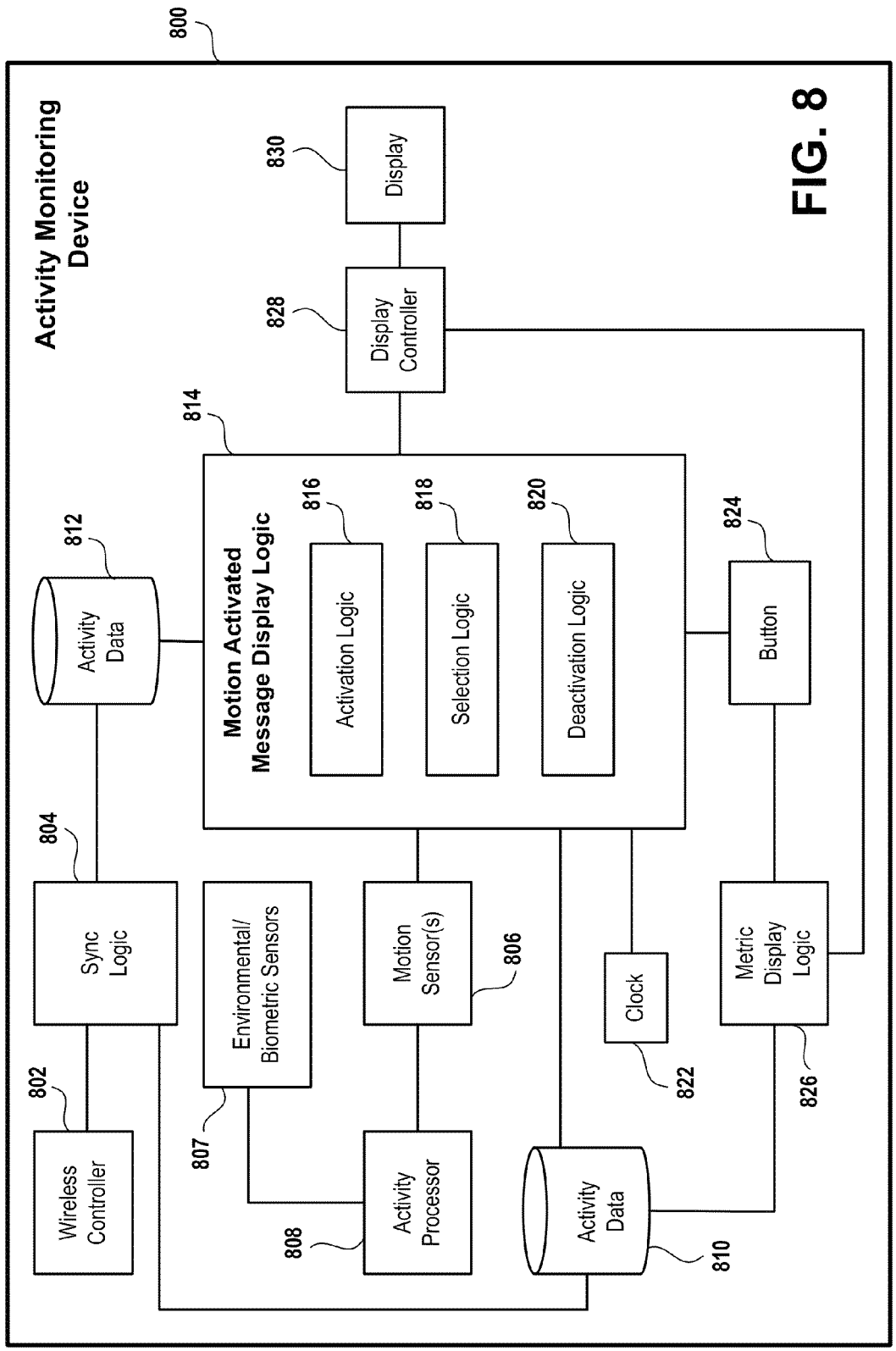
FIG. 8 conceptually illustrates components of an activity monitoring device, in accordance with an embodiment of the invention.

FIG. 8 conceptually illustrates components of an activity monitoring device, in accordance with an embodiment of the invention. As shown, the activity monitoring device 800 is defined to include motion sensors 806, which may include, without limitation, accelerometers, gyroscopes, magnetometers, motion sensitive contact switches, or other motion-sensing hardware. Additionally, the device 800 can include other environmental or biometric sensors 807, as discussed elsewhere herein. An activity processor 808 processes sensor output data generated by the sensors 806 and 807 to determine activity by the user, such as a number of steps taken, changes in altitude, periods of activity or inactivity, calories burned, etc. These activity data are stored in an activity data storage 810. It will be appreciated that raw sensor data can also be stored for later processing.

The device 800 further includes a motion activated message data storage 812 which contains message data defining various messages that can be presented based on motion of the device following a detected stationary state. Motion activated message display logic 814 is configured to determine when to display a motion activated message as well as the particular message that is displayed. The motion activated message display logic 814 includes activation logic 816. In one embodiment, the activation logic 816 is configured to identify, based on sensor data received from the motion sensors 806, when the device 800 is resting in a predefined orientation. As has been discussed, the predefined orientation may correspond to various possible resting orientations of the device 800 when it is placed on a substantially horizontal flat surface.

The activation logic 816 determines when the device 800 is continuously oriented in the predefined orientation for a specified minimum period of time. By way of example, the specified minimum period of time may be defined in the range of 2 to 5 seconds, 5 to 10 seconds, 10 seconds to 1 min., 1 to 10 min., or any other defined period of time. In one embodiment, the specified minimum period of time may be determined based on a user defined setting. In yet another embodiment, the specified minimum period of time may vary depending upon various factors, such as time of day, the amount of activity or inactivity recently associated with the device 800, etc.

When the activation logic 816 determines that the device 800 has continuously maintained the predefined orientation for the requisite minimum period of time, then the activation logic 816 is configured to detect a subsequent movement of the device 800 from the predefined orientation, based on sensor data from the motion sensors 806. Upon such detection of movement, the activation logic is configured to trigger selection and display of a motion activated message on the device 800.

In various embodiments, it will be appreciated that the activation logic 816 can be configured to consider other factors or purposes of determining when to trigger selection and display of a motion activated message. For example, a user interacting with the device 800 may place the device 800 on a flat surface while its display is still active. A timer can be configured to automatically turn off the display after a given amount of time in which interactivity with the display is not detected (e.g. a button on the device 800 which controls the operation of the display is not pressed). Thus in one embodiment, the activation logic 816 is configured to determine a current active or inactive state of the display 830, and does not commence its procedure for determining when to trigger the motion activated message unless the display is currently inactive or turned off.

In another embodiment, the activation logic 816 will not commence its activation procedure unless ambient light levels detected by the device 800 are above a predefined threshold. This may prevent the unnecessary display of a motion activated message when the device 800 is in a dark location, such as a pocket of a user, or a purse or bag, by way of example.

In another embodiment, the activation logic 816 will not trigger a motion-activated message during a time period for which an event is scheduled in a calendar of the user, such as a meeting or other type of event. This will prevent the display of motion-activated messages when the user is scheduled, and therefore expected, to be preoccupied with some activity. In one embodiment, this is facilitated via synchronization operations between the device 800 and another computing device which includes a calendar for the user, such as a smart phone or computer. During synchronization operations, the calendar of the user (on the additional device to which the device 800 syncs) is accessed to determine event scheduling information. This information defines time periods for events which have been scheduled on the calendar. At least the start and end times for the scheduled events can be transmitted to the device 800 and utilized to define time periods during which motion-activated messages will not be displayed.

In another embodiment, the activation logic 816 is configured to not trigger a motion-activated message when it is determined that the user is engaged in an activity during which it is expected that the user will be unavailable to view a motion-activated message. For example, in one embodiment, if it is determined that the device is currently moving in a motor vehicle such as a car (e.g. based on GPS data and/or motion data), the activation logic 816 may be configured to not trigger a motion-activated message.

When the activation logic 816 determines that a motion activated message is to be displayed, as discussed above, then selection logic 818 is engaged to select a message from the message data storage 812 for presentation. The selection logic 818 can be configured to select the message based on a variety of factors as discussed elsewhere herein. By way of example, the device 800 includes a clock 822, which provides a current date and time, which may be utilized by the selection logic 818 to determine which message to present. In one embodiment, the selection logic 818 determines a ranked order for a plurality of messages stored in the message data storage 812, and identifies a specific message for presentation based on the ranked order. The motion activated message display logic 814 is configured to render the selected message on the display 830 of the device 800 via a display controller 828.

The motion activated message display logic 814 further includes deactivation logic 820 which is configured to deactivate the operation of the display logic 814 under certain conditions. For example, when a user presses a button 824 to interact with the device 800, this may trigger deactivation logic 822 to deactivate the message display logic 814. As discussed herein, input received from the button 824 may trigger the display of various activity metrics by metrics display logic 826. Thus, pressing the button 824 will cause any motion activated message that is currently displayed on the display 830 to be replaced by various metrics or other information, the display of which is triggered by a button press.

In other embodiments, the display of a motion activated message can be terminated in response to other types of interaction or the lack thereof. For example, a motion activated message may be configured to be displayed for a limited amount of time, whereupon if no additional interaction with the device 800 is detected, then rendering of the motion activated message is terminated, and the display is turned off. In such an embodiment, the deactivation logic 820 can be configured to include a timer that is activated when a motion activated message is rendered by the display logic 814. Upon the expiration of the timer, then the display of the motion activated message is stopped. In a related embodiment, upon the expiration of a limited amount of time, the display of the motion activated message is ended and replaced with display of other information automatically, such as a current time, activity metric, or any other information which the device 800 may be configured to display.

In another embodiment, the display of a motion activated message is terminated upon the detection of a specific kind of physical interaction with the device 800, e.g. shaking the device, tapping the device, touching or swiping a touchscreen on the device, etc. Additionally, these types of physical interactions with the device 800 can be configured to trigger display of other information replacing the previously displayed motion activated message on the display 830.

The device 800 also includes synchronization logic 804 which is configured to handle synchronization of data with another device or with a remote server or cloud-based service. The activity monitoring device 800 is configured to wirelessly transmit and receive data, with wireless communications being handled by a wireless controller 802. Synchronization logic 804 is configured to upload activity data from the activity data storage 810. The synchronization logic 804 is also configured to download motion activated message data from a remote storage location to the motion activated message data storage 812. In this manner, the synchronization logic 84 updates the messages which are stored in the message data storage 812. It should be appreciated that the synchronization logic 804 may also be configured to effect deletion of messages from the motion activated message data storage 812.

Figure 9:
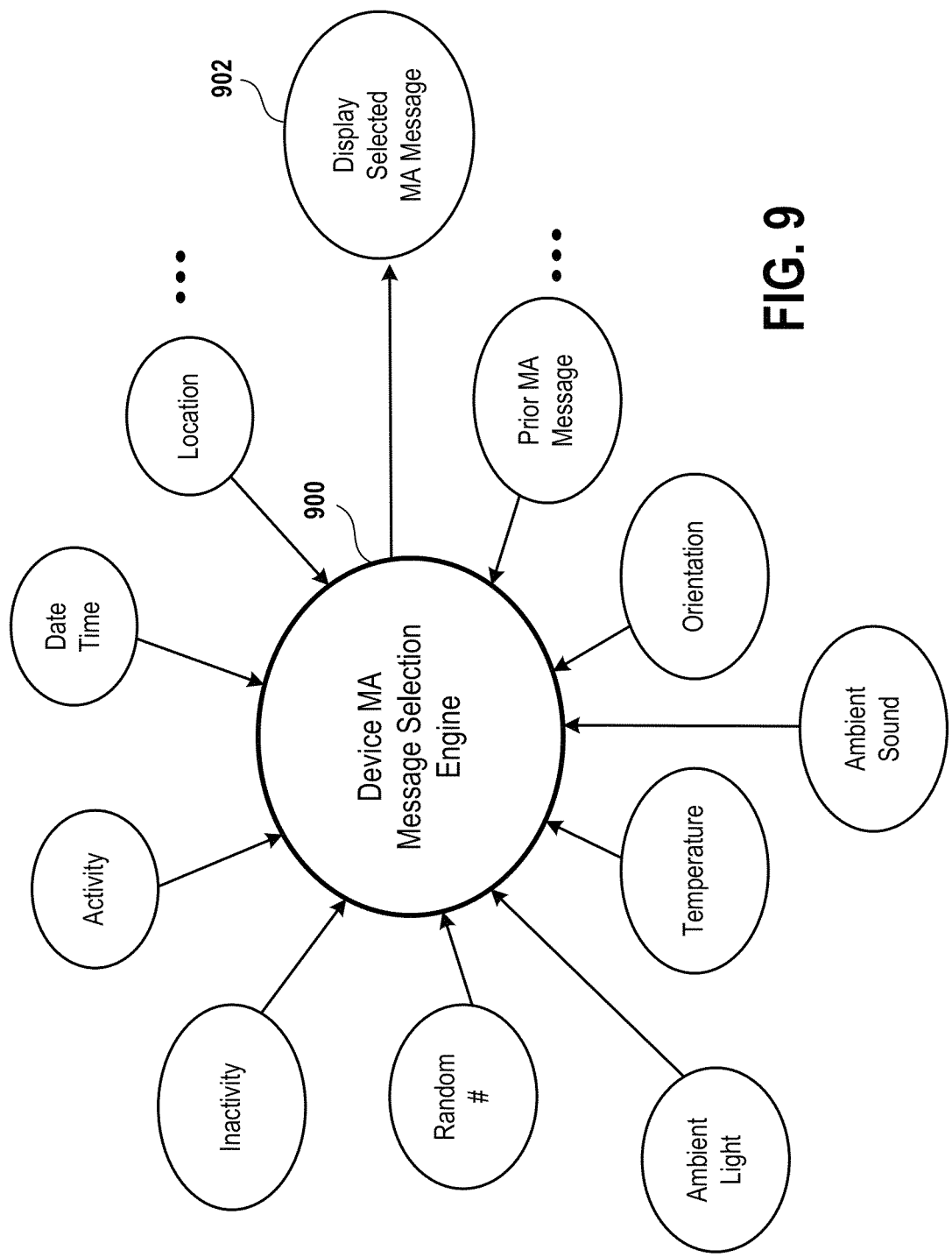
FIG. 9 conceptually illustrates selection of a motion activated message at an activity monitoring device based on a variety of factors, in accordance with an embodiment of the invention.

FIG. 9 conceptually illustrates selection of a motion activated message at an activity monitoring device based on a variety of factors, in accordance with an embodiment of the invention. In the illustrated embodiment, a device motion activated message selection engine 900 is shown. The message selection engine 900 is configured to select a message for display on an activity monitoring device (ref. 902) in response to detection of movement of the device from a predefined stationary orientation.

In one embodiment, a message may be selected based on a current time of day. For example, a message such as "good morning" may be selected when the current time is in the morning. A message may also be selected based on the current date or day of the week. For example, a message such as "TGIF" may be selected on a Friday. In another embodiment, a message may be selected based on a current location of the device. For example, if the user travels to a new location such as the city of San Francisco, then a message may be configured to welcome the user to the new location, such as "welcome to San Francisco."

In one embodiment, a message may be selected based on the activity of a user as determined via the activity monitoring device. For example, if the user has recently been determined to have taken a certain number of steps, then a message may be selected congratulating the user on having taken that many steps. In message may also be selected based on the inactivity of the user is determined by the activity monitoring device. For example, if the device has been resting without movement for an extended period of time, then a message may be selected that is configured to encourage the user to engage in fitness activity or otherwise engage with the device, such as "walk me."

In one embodiment, a message may be selected at random, or based on a random number. In another embodiment, a message may be selected based on prior message selection, so as to avoid displaying the same message to the user in a relatively short time span.

In some embodiments, a message may be selected for display based on various sensed conditions. For example, a message may be selected based on an environmental condition which the activity monitoring device is capable of detecting, such as ambient light, temperature, ambient pressure, altitude, humidity, ambient sound, orientation, etc.

Figure 10:
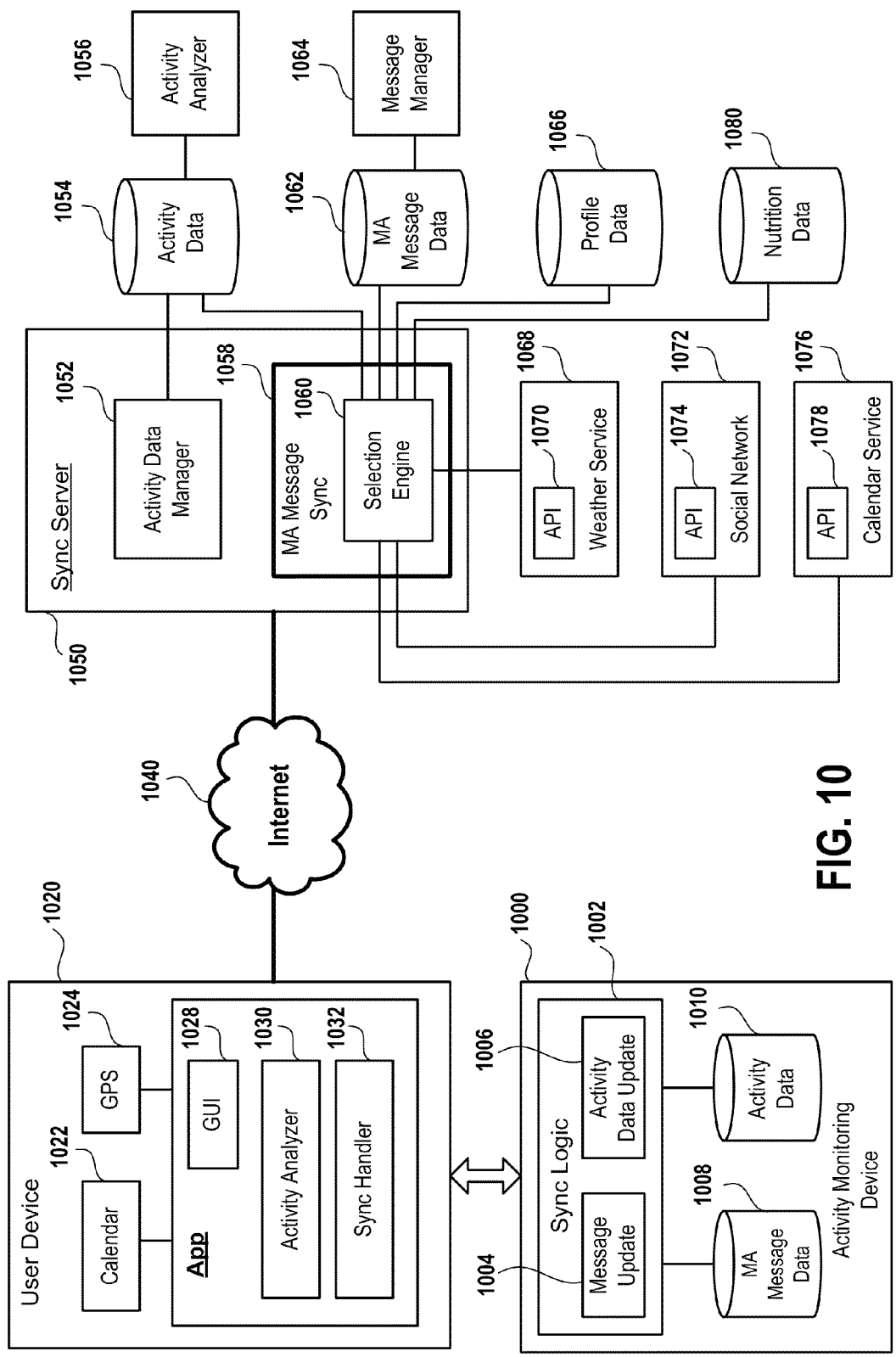
FIG. 10 conceptually illustrates a system for determining motion activated messages to be presented on an activity monitoring device, in accordance with an embodiment of the invention.

FIG. 10 conceptually illustrates a system for determining motion activated messages to be presented on an activity monitoring device, in accordance with an embodiment of the invention. An activity monitoring device 1000 is shown to include synchronization logic 1002. The synchronization logic 1002 includes a message update module 1004 that is configured to update motion activated message data that is stored in a motion activated message data storage 1008. The synchronization logic 1002 further includes an activity data update module 1006 that is configured to manage activity data stored in the activity data storage 1010, including uploading of activity data as well as deletion of activity data in accordance with the embodiments described herein.

The activity monitoring device 1000 communicates to a user device 1020, that in turn communicates with a remote server 1050 via a network 1040. The user device 1020 may be a mobile device or any other type of computing device capable of performing the functionality described herein. In the illustrated embodiment, the user device 1020 includes a calendar module 1022 that is configured to maintain a personal calendar of the user. The calendar may be synchronized to a cloud-based calendar service 1074, which may be accessed via a calendar API 1076. Additionally, the user device 1020 includes a GPS module 1024 that is configured to determine a geo-location of the user device 1020.

The user device 1020 includes an application 1026, which may be a browser or a dedicated application that is configured to interface with the activity monitoring device 1000 as well as the server 1050. The application 1026 defines a graphical user interface 1028 through which the user may control the operation of the application 1026. The application 1026 further defines an activity analyzer 1030 which is configured to analyze activity data received from the activity monitoring device 1000. A synchronization handler 1032 is configured to handle synchronization operations between the activity monitoring device, the user device 1020, and cloud-based data storage accessed via the server 1050. For example, the sync handler 1032 may communicate with the activity data update module 1006 defined by the sync logic 1002 of the activity monitoring device 1000 in order to facilitate uploading of activity data from the activity monitoring device 1000 to the user device 1020. The uploaded activity data may be further processed by the activity analyzer 1030, and/or may be transmitted via network 1040 to an activity data manager 1052 of the server 1050, for storage in a cloud-based activity data storage 1054. An activity analyzer 1056 of the cloud-based system is configured to analyze the activity data stored in the activity data 1054, and may generate additional activity data that are also stored in the activity data storage 1054.

The server includes a motion-activated message synchronization module that is configured to select messages and download them to the activity monitoring device. The downloading of selected messages is mediated by the sync handler 1032 of the user device 1020, with which a message update module 1004 of the activity monitoring device 1000 communicates to receive message data for storage in the message data storage 1008. In other words, the message data is transferred from the server 1050 to the user device 1020, and the user device 1020 in turn transfers the message data to the activity monitoring device for storage. In this manner, the motion activated message data on the activity monitoring device is updated by the remote server 1050. It should be appreciated that the transfers of the message data may occur in immediate succession when the user device 1020 is simultaneously connected to both the server 1050 and the activity monitoring device 1000. However, when the user device 1020 is not connected to the activity monitoring device 1000, then message data may be transferred by the server 1050 to the user device 1020 and temporarily stored at the user device 1020 until the activity monitoring device is connected to the user device 1020, at which time the message data may then be transferred to the activity monitoring device 1000.

In addition to transfers of message data defining specific motion activated messages to the activity monitoring device 1000, the motion activated message synchronization module 1058 of the server 1050 may additionally be configured to effect other changes to the message data stored at the activity monitoring device 1000. For example, commands or updates may be sent to the activity monitoring device 1002 to manage the message data stored in the message data storage 1008. Examples of such commands or updates include, without limitation, deletion of messages, modification of messages, changes to metadata associated with messages, etc.

In the illustrated embodiment, the message synchronization module 1058 includes a message selection engine 1060 that is configured to select one or more messages to be transferred to the activity monitoring device 1000. A plurality of messages that are available for selection are stored in a message data storage 1062. A message manager 1064 is provided for managing the messages stored in the message data storage 1062. In one embodiment, the message manager 1064 provides an interface whereby an editor may create new messages, or edit or delete existing messages.

The selection engine 1060 is configured to select messages based on a variety of factors. By way of example, selection engine 1060 can be configured to identify selected messages based on activity data that is associated with the activity monitoring device 1000, as stored in the activity data storage 1054. Such activity data can include various fitness metrics and other types of data which are determined based on the monitored activity of the activity monitoring device 1000. The selection engine 1060 may also select messages based on the user profile associated with a user of the activity monitoring device 1000. In the illustrated embodiment, the user profile may be defined in a profile data storage 1066. By way of example and not limitation, a user profile may define various pieces of information about a given user, such as the user's age, gender, residence, height, weight, preferences, etc. The user profile can include a historical activity profile of the user based on the user's activity data and fitness metrics. In this manner, different messages may be selected based on, for example, whether the user is historically more sedentary or more active.

It will be appreciated that activity data may be defined by values, levels, metrics, etc. of particular activities which are associated to specific times or time periods. The activity data which are recorded over time can therefore define an activity history for a given user. It is noted that the granularity of such time associations may vary in accordance with the specific activity being tracked or other considerations such as a predefined goal or, a predefined threshold for defining or triggering a motion-activated message. As one example of an activity whose levels may be defined with varying time-associated granularity, consider that a user's stepcount might be determined on a per minute basis, per hour, per day, per week, per month, etc. Furthermore, a predefined threshold might be defined so that a motion-activated message is defined or triggered (i.e. selected or cued for motion-activated display) when the user achieves a given number of steps in a given time period (e.g. x number of steps in a day). As another example, a user's heart rate may be monitored over the course of a given time period, and a corresponding motion-activated message can be defined or triggered based on the user's heart rate data. It should be understood that similar concepts may be applied for any other activity discussed herein.

Thus in some embodiments, an activity history for a given user can define levels of activity that are associated to specific time periods, as determined from data recorded by a given activity tracking device to which the user is associated. Motion-activated messages can be defined and/or triggered based on the activity history of the user. In this manner, the motion-activated messages that are presented to the user are customized to the user's activity history, thereby providing a personalized experience the user.

In one embodiment, the message selection engine 1060 can be configured to select messages based on nutrition data which is stored in a nutrition data storage 1080. The nutrition data for a given user can include information about the user's nutrition, such as meal information including foods/drinks that the user has consumed and the times they were ingested, diet plan information, etc.

In one embodiment, the selection engine 1060 is configured to identify selected messages for transfer to the activity monitoring device 1000 based on current or predicted weather information. The weather information can be obtained from a weather service 1068, via an API 1070 according to which weather information is made available.

In one embodiment, the message selection engine 1060 is configured to identify selected messages based on social network data that is associated with the user of the activity monitoring device 1000. In the illustrated embodiment, the social network data can be obtained from a social network service provider 1072 via an API 1074. By way of example, social network data can include activity of the user on the social network, such as posts or comments, as well as information relating to the social graph of the user on the social network, such as identified friends of the user from the user social graph and their activity on the social network.

In one embodiment, the selection engine 1060 is configured to select messages based on calendar events that are associated with the user of the activity monitoring device 1000. In order to determine calendar events, a calendar service 1076 may be accessed via an API 1078. The calendar service 1076 is configured to maintain a calendar associated with the user that defines various events and their dates/times.

Though in the foregoing description, the activity monitoring device 1000 is shown to communicate with a user device 1020, which in turn communicates with the server 1050 over a network 1040, in other embodiments, some or all of the functionality defined by the user device 1020 may be included in or otherwise performed by the activity monitoring device 1000. Thus, in such embodiments, the activity monitoring device itself may communicate directly with the server 1050 over the network 1040 in order to perform data synchronization and other operations such as downloading selected messages to the activity monitoring device 1000, as has been described.

Figure 11:
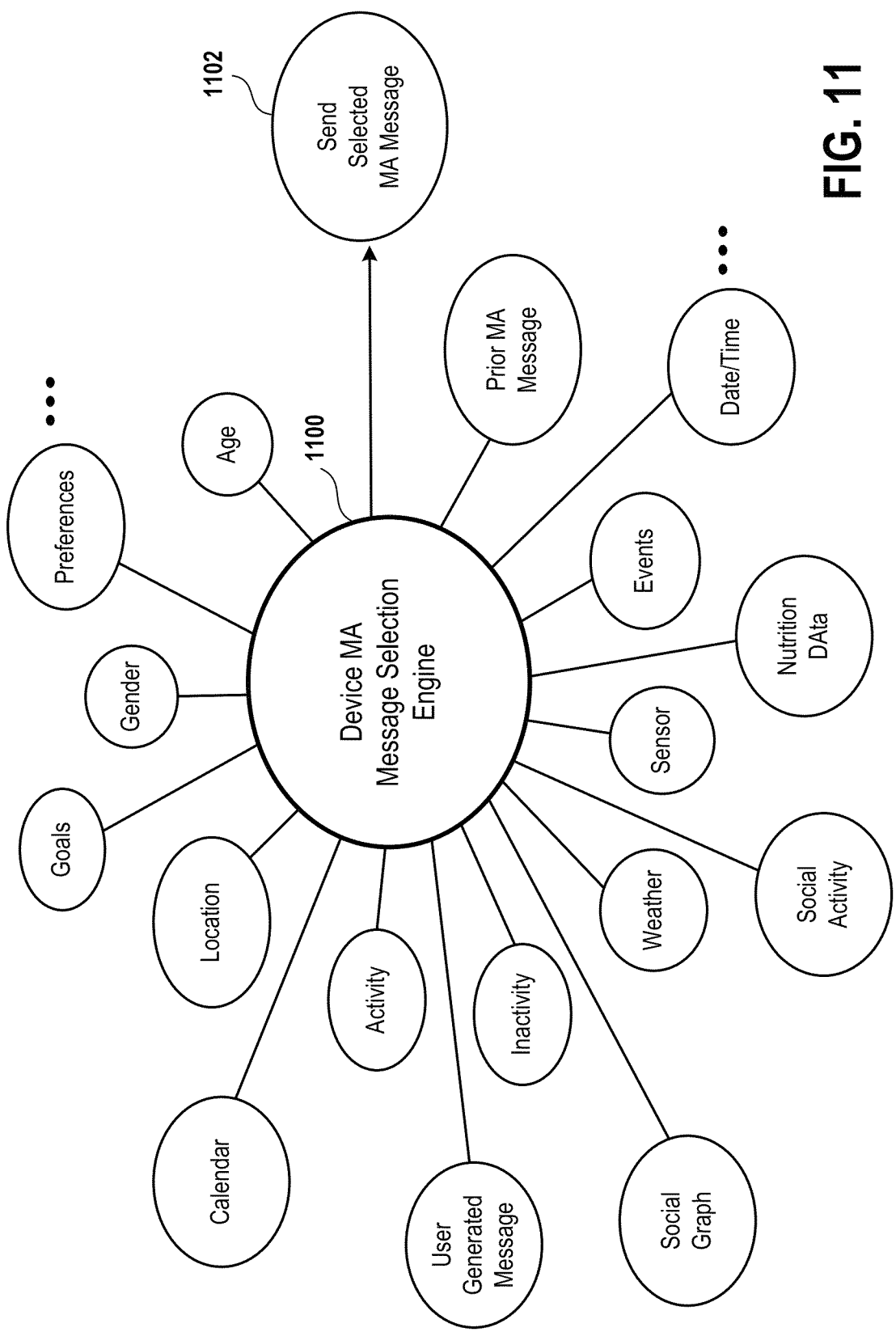
FIG. 11 conceptually illustrates various factors which may be considered for purposes of selecting one or more messages to be sent to an activity monitoring device for display in response to motion activation, in accordance with an embodiment of the invention.

FIG. 11 conceptually illustrates various factors which may be considered for purposes of selecting one or more messages to be sent to an activity monitoring device for display in response to motion activation, in accordance with an embodiment of the invention. In the illustrated embodiment, a server-side motion activated message selection engine 1100 is configured to select messages based on various factors or inputs. The selected messages are sent to an activity monitoring device (ref. 1102).

In one embodiment, the selection engine 1100 is configured to identify messages for selection based on demographic data associated with a user of the activity monitoring device, such as age, gender, ethnicity, height, weight, medical conditions, etc. For example, age-appropriate messages may be selected based on the user's age. In one embodiment, the selection engine 1100 is configured to select messages based on an identified location of the user. The location can be defined to varying degrees of specificity, such as by identifying a country, state, city, address, landmark, business, GPS coordinates, or other information which defines a location of the user. The location can be a current location of the user, or another location associated with the user, such as a residence or work address. By way of example, messages in the appropriate language may be provided based on location information. Or messages may reflect aspects of the locality of the user. For example, if the user is determined to be located near a park, then a message may be selected which encourage the user to go for a walk or run in the park.

In one embodiment, the selection engine 1100 is configured to select messages based on preferences or settings which are associated to the user. These may include, without limitation, fitness metric preferences such as which fitness metrics the user prefers, activity interests associated with the user, etc.

In one embodiment, the selection engine 1100 is configured to select messages based on fitness-related goals which may be user-defined goals or system-identified milestones. For example, a message may congratulate the user on achieving a goal, or encourage a user to perform activity in furtherance of a goal/milestone. Examples of goals include, without limitation, walking a certain number of steps, burning a certain number of calories, accruing a certain number of active minutes, climbing a certain height (possibly represented by an equivalent number of stairs/floors), etc.

In one embodiment, the selection engine 1100 is configured to select messages based on events stored in a calendar associated with the user. For example, such a message may be configured to remind the user about an upcoming calendar event, ask the user about a current or prior event, etc.

In one embodiment, the selection engine 1100 is configured to select messages based on activity or inactivity of the user, as detected by the activity monitoring device. For example, if the user has been very active recently, then a selected message may congratulate the user on the activity, encourage the user to get rest/sleep, or encourage the user to eat appropriately. If the user has been rather inactive recently, then a selected message may encourage the user to engage in physical fitness activity.

In one embodiment, the selection engine 1100 is configured to select messages based on the current or predicted weather. For example, a message may recommend clothing or accessories which are appropriate for the day's weather (e.g. hat/sunglasses for sunshine, umbrella for rain, gloves/scarf for cold weather), recommend activities based on the weather (e.g. "it's a nice day for a walk"), etc.

In one embodiment, the selection engine 1100 is configured to select messages based on the current season. For example, during particular holidays or seasons, messages may be selected which are indicative of those holidays or seasons (e.g. "happy labor day"; "spring is in the air").

In one embodiment, the selection engine 1100 is configured to select messages based on events occurring. For example, a message may ask or inform a user about an upcoming fitness-related event (e.g. a 10K run), or other types of events (e.g. concerts, sporting events, festivals, shows, etc.).

In one embodiment, the selection engine 1100 is configured to select messages based on the current date or time, day of the week, month, or other indicator of time.

In one embodiment, the selection engine 1100 is configured to select messages based on previously selected messages which have been transferred to the activity monitoring device. For example, messages which have been recently transferred may not be selected so as to avoid duplication.

In one embodiment, the selection engine 1100 is configured to select messages based on nutrition data associated with the user.

In one embodiment, the selection engine 1100 is configured to select messages based on data or activity of the user on a social network, or that of members of the user's social graph. For example, social activity of the user may indicate an interest in basketball, and a message relating to basketball may be selected.

In one embodiment, a message may be generated by a secondary user, to be presented as a motion-activated message on the primary user's activity monitoring device, as discussed in further detail below. Such a message may be prioritized for transmission to the primary user's activity monitoring device.

It will be appreciated that the foregoing examples of factors according to which messages may be selected for transmission to an activity monitoring device, are provided by way of example and not by way of limitation. In other embodiments, additional factors may be considered by a message selection engine in accordance with the principles described herein.

Figure 12:
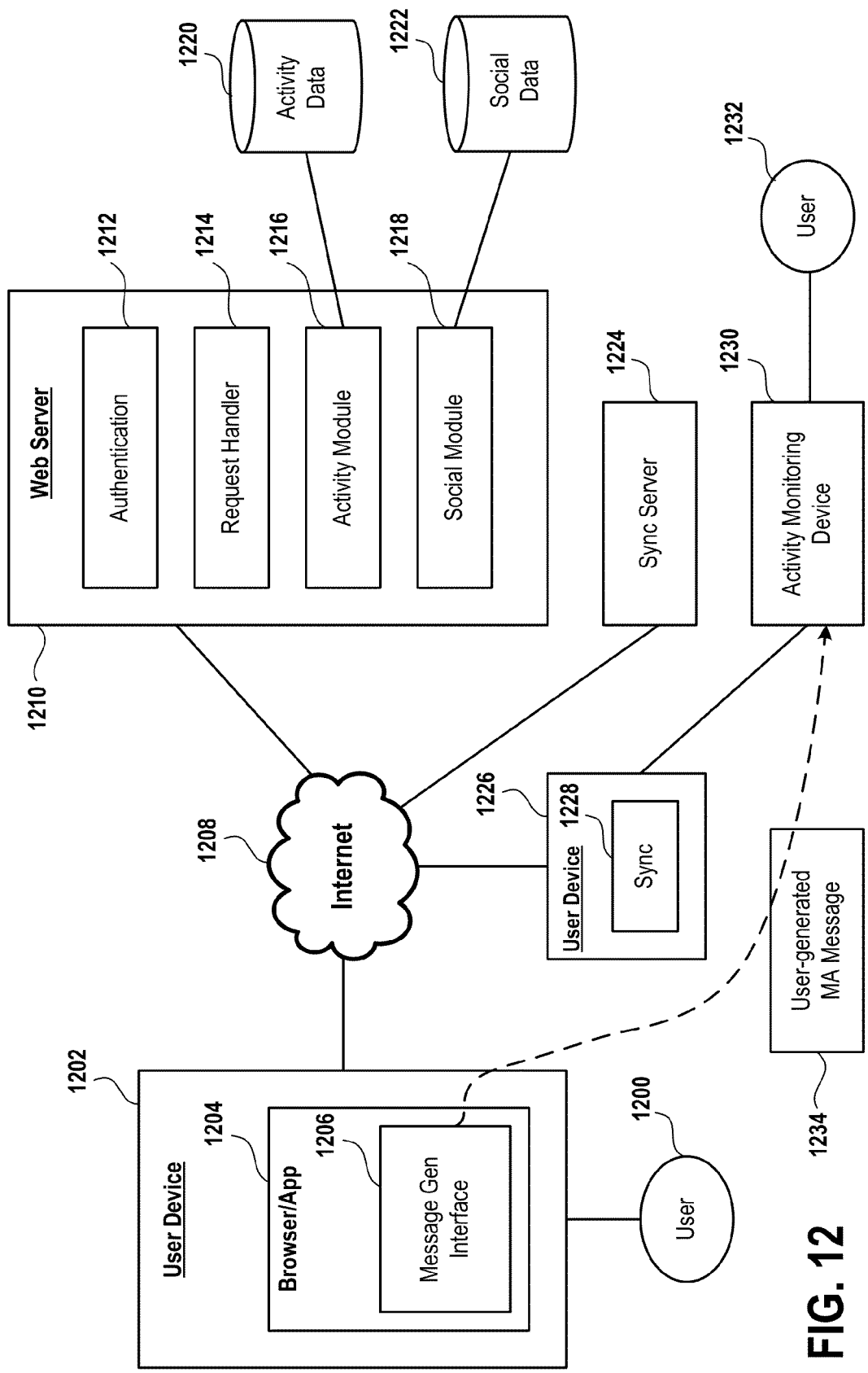
FIG. 12 illustrates a system for enabling a first user to generate a message that will be displayed to a second user in response to motion of an activity monitoring device of the second user, in accordance with an embodiment of the invention.

FIG. 12 illustrates a system for enabling a first user to generate a message that will be displayed to a second user in response to motion of an activity monitoring device of the second user, in accordance with an embodiment of the invention. In the illustrated embodiment, a user 1200 interacts with the user device 1202. The user device 1202 can be any computing device, and as shown, includes an application or browser 1204 that is configured to access a user account which may define activity information as well as social network information associated with the user 1200. For purposes of illustration, a web browser type implementation is described, though it should be appreciated that in other embodiments, a dedicated application can be configured to enable the functionality described herein.

The browser 1204 communicates over a network 1208 to a Web server 1210. The Web server 1210 includes an authentication module 1212 that is configured to authenticate the user 1200 to their account. A request handler 1214 is provided for servicing requests from the browser 1204. Activity module 1216 is provided for accessing and managing activity data associated with the user 1200 that is stored in the activity data storage 1220. Additionally, a social module 1218 is provided for accessing and managing social data associated with the user 1200 that is stored in a social data storage 1222 it should be appreciated that the user 1200 may have access to activity data as well as social data associated with members of the user's social graph.

The browser 1204 communicates with the Web server 1210 to provide an interface on the user device 1202 whereby the user 1200 can access their activity data and social data, and perhaps view related activity of their friends on their social network. In one embodiment, the browser may access and present a message generation interface 1206 which may be utilized by the user 1200 generate a custom message to another user 1232. The message generation interface 1206 can be configured to allow the user 1200 to enter text or other types of messaging data to define a custom user-generated message 1234. The user-generated message 1234 is provided to an activity monitoring device 1230 associated with the user 1232 in accordance with embodiments previously described herein. For example, the activity monitoring device 1230 may communicate with a user device 1226 having a synchronization module 1228, which in turn communicates with a synchronization server 1224 to effect downloading of the user generated message 1234 to the activity monitoring device 1230. Then, when the activity monitoring device 1230 is placed in a predefined stationary state, the user generated message 1234 may be displayed when the activity monitoring device 1230 is subsequently moved from the stationary state.

Figure 13:
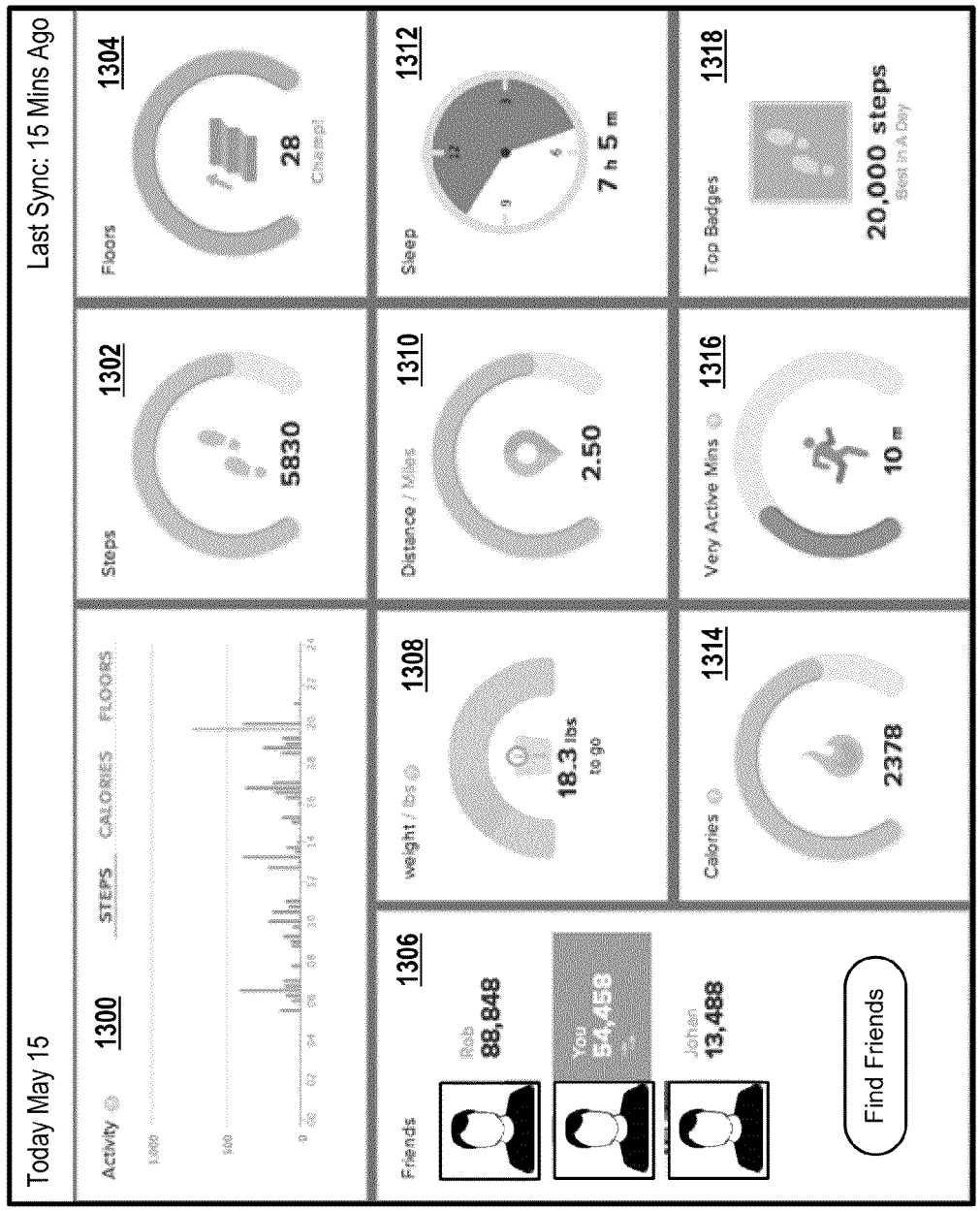
FIG. 13 illustrates an interface for accessing activity data associated with the user of an activity monitoring device, in accordance with an embodiment of the invention.

FIG. 13 illustrates an interface for accessing activity data associated with the user of an activity monitoring device, in accordance with an embodiment of the invention. Broadly speaking, the illustrated interface is defined by various components or tiles which are configured to display activity related information. It should be appreciated that the illustrated components provided merely by way of example and not limitation, and that in other embodiments, additional components or types of information can be presented through an interface to the user.

A recent activity module 1300 provides a graph illustrating recent activity recorded by the activity monitoring device of the user. As shown, various selectable options enable the user to view the number of steps they have recently taken, calories burned, or floors climbed. A steps module 1302 is configured to present a number of steps which have been taken by the user. It will be appreciated that the number of steps may be counted for a limited time period, such as the number of steps taken during the current day or current week. The steps module 1302 can also be configured to graphically illustrate the number of steps taken in relation to a goal or some predefined milestone or threshold, or a number of steps remaining to reach the goal or milestone.

A floors climbed module 1304 is configured to present a number of floors climbed within a given time period. It should be appreciated that the number of floors climbed is a conversion indicative of altitude changes that have been detected by the activity monitoring device. For example, if the activity monitoring device detects that the user has ascended a total of 100 feet and each floor is defined as the equivalent of 10 feet, then the 100 feet of ascension will be represented as a climb of 10 floors. The floors module 1304 can also be configured to indicate the relationship between the number of floors climbed and a goal, as well as the number of floors remaining to reach said goal.

A friends module 1306 is configured to display friends of the user from the user's social graph. Activity data associated with the user's friends can also be shown. In one embodiment, the user may access a message generation interface from the friends module 1306 to generate a custom user-defined message for display at the friend's activity monitoring device in response to movement from a stationary state, in accordance with the principles described herein. By way of example, clicking on or otherwise selecting a specific friend is presented in the friends module 1306 may provide access to options including an option to generate the custom motion activated message.

A weight module 1308 is configured to present a weight of the user, or a weight remaining to be lost by the user, or other weight related information. The distance module 1310 is configured to present a distance traveled by the user as measured based on data obtained from the user's activity monitoring device. The sleep module 1312 is configured to display an amount of sleep which the user has attained. A calories module 1314 is configured to display a number of calories burned by the user. A very active minutes module 1316 is configured to display the number of minutes of very active or vigorous activity by the user. A top badges module 1318 is configured to display badges or goals or milestones which the user has achieved. It will be appreciated that any of the foregoing modules may be configured to display specific metrics in relation to predefined goals, or amounts remaining to achieve such goals.

Though various embodiments have been described with reference to motion-activated messages which consist of text, it should be appreciated that the concepts relating to motion-activated messages may also apply to other forms of information which may be displayed or otherwise rendered in response to detected movement of an activity monitoring device from a stable stationary position. For example, a motion-activated "message" may be defined by an image, video, audio, animation, haptic event, or any other type of information or communicative event that may be presented through an activity monitoring device in accordance with embodiments of the invention.

In the foregoing embodiments, messages have been displayed on an activity monitoring device in response to detected movement of the device from a stationary position defined by a predefined orientation. However, in other embodiments, a message may be configured to be displayed on the activity monitoring device in response to other types of changes which are detectable by the activity monitoring device.

Broadly speaking, the activity monitoring device can be configured to display a message in response to detecting a change from a non-user interactive state to a user interactive state. In embodiments presented above, the non-user interactive state can be defined by a stationary state in which non-movement of the device for a predefined period of time is detected. A change to a user-interactive state is detected when a movement of the device from the stationary state is detected.

In another embodiment, a change from a non-user interactive state to a user interactive state can include detecting a movement of the device from a first orientation to a second orientation, or detecting a predefined motion or movement of the device. For example, in an embodiment where the activity monitoring device is worn on a user's wrist, when the user maneuvers his/her arm to view the display on the activity monitoring device, such a movement or change in orientation can be detected, and in response, a message may be displayed. In another embodiment, the motion of the user flicking their wrist may be detected, and a message can be displayed in response.

The concept can be further extended to encompass different detected activity states, wherein the non-user interactive state might be defined by a particular detected physical activity state of the user (e.g. running, cycling, etc.). If the user moves or re-orients the device so as to be able to view its display, then such a movement or re-orientation may be detected, and a message displayed in response.

In another embodiment, the non-user interactive state can include detecting a charging state of the device, wherein the device is connected to a charger. The change to the user-interactive state can be defined by detecting a change of the device from the charging state to a non-charging state, wherein the device is disconnected from the charger.

In still other embodiments, the change from the non-user interactive state to the user-interactive state can be defined by detected actions, such as a button press or an interaction with a touchscreen (e.g. touch, swipe, gesture, etc.).

In another embodiment, a message may be displayed in response to a change in temperature detected at the activity monitoring device. Such a message may be displayed in response to a change in the temperature having a magnitude greater than or equal to a predefined threshold, either an increase or a decrease in temperature. In a related embodiment, a message may be displayed in response to detection by the activity monitoring device of a specific ambient temperature. In this manner, message display is triggered by reaching specific ambient temperatures.

In another embodiment, a message can be configured to be displayed in response to changes in ambient light levels. For example, a sudden change from very low ambient light levels to comparatively high ambient light levels may indicate that the activity monitoring device has been removed from the user's pocket or otherwise taken out of a dark location for viewing by the user. Hence, the activity monitoring device may be configured to display a message in response to detection of such a change in ambient light.

In another embodiment, the activity monitoring device may be configured to display a message in response to changes in ambient sound levels.

The aforementioned methods and systems for displaying motion-activated messages on an activity monitoring device serve to improve the user experience of interacting with the activity monitoring device. By displaying messages in response to motion from a stationary state, the activity monitoring device can react to the user's intent to interact with or otherwise utilize the device, as indicated by the motion. Furthermore, by intelligently selecting messages for display in a manner that is customized for the individual user, the experience can be highly personalized, and thus may appear to imbue the activity monitoring device with an apparent voice or persona.

Figure 14:
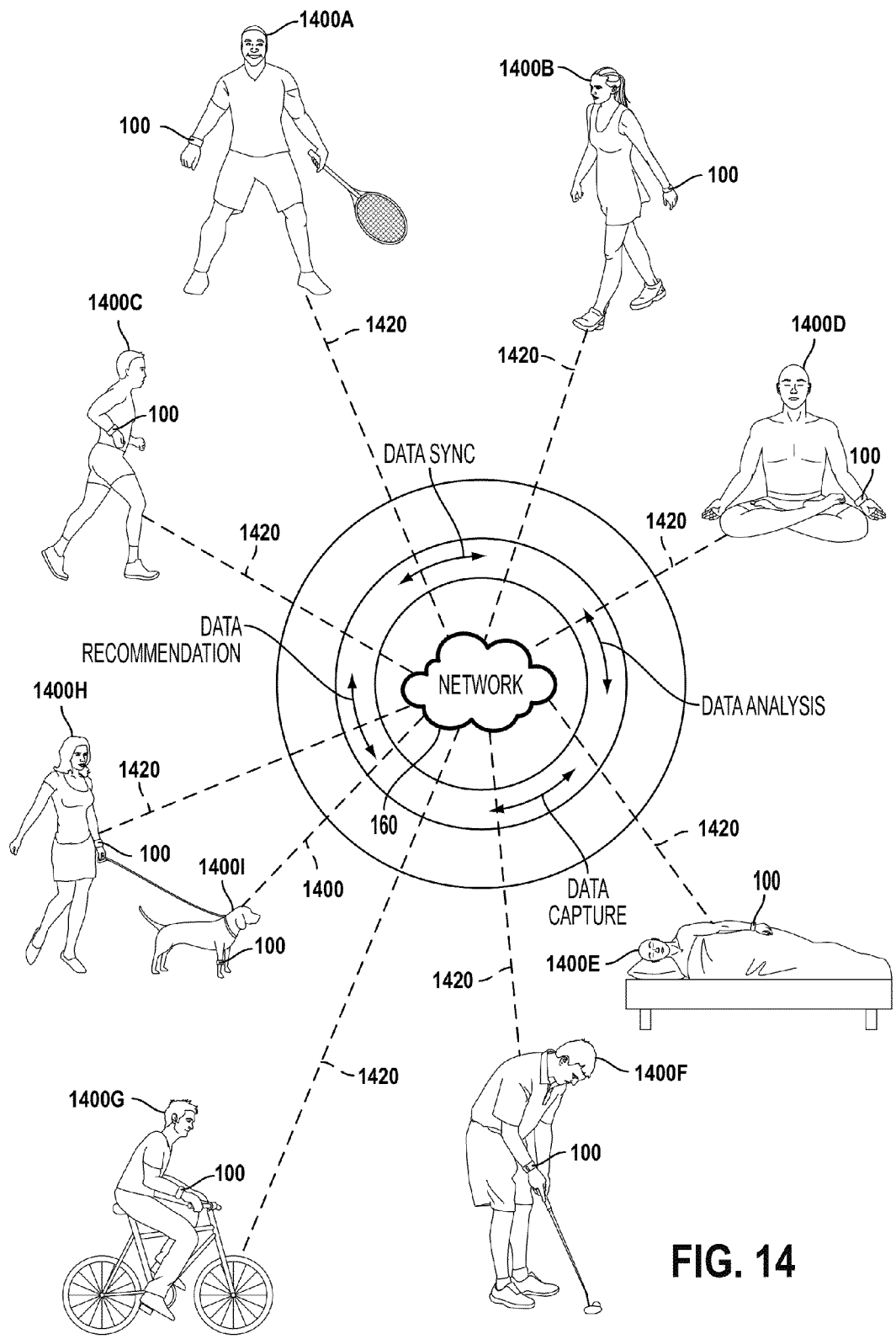
FIG. 14 illustrates an example where various types of activities of users can be captured or collected by activity tracking devices, in accordance with various embodiments of the present invention.

FIG. 14 illustrates an example where various types of activities of users 1400A-1400I can be captured by activity tracking devices 100, in accordance with one embodiment of the present invention. As shown, the various types of activities can generate different types of data that can be captured by the activity tracking device 100. The data, which can be represented as motion data (or processed motion data) can be transferred 1420 to a network 176 for processing and saving by a server, as described above. In one embodiment, the activity tracking device 100 can communicate to a device using a wireless connection, and the device is capable of communicating and synchronizing the captured data with an application running on the server. In one embodiment, an application running on a local device, such as a smart phone or tablet or smart watch can capture or receive data from the activity tracking device 100 and represent the tract motion data in a number of metrics.

In one embodiment, the device collects one or more types of physiological and/or environmental data from embedded sensors and/or external devices and communicates or relays such metric information to other devices, including devices capable of serving as Internet-accessible data sources, thus permitting the collected data to be viewed, for example, using a web browser or network-based application. For example, while the user is wearing an activity tracking device, the device may calculate and store the user's step count using one or more sensors. The device then transmits data representative of the user's step count to an account on a web service, computer, mobile phone, or health station where the data may be stored, processed, and visualized by the user. Indeed, the device may measure or calculate a plurality of other physiological metrics in addition to, or in place of, the user's step count.

Some physiological metrics include, but are not limited to, energy expenditure (for example, calorie burn), floors climbed and/or descended, heart rate, heart rate variability, heart rate recovery, location and/or heading (for example, through GPS), elevation, ambulatory speed and/or distance traveled, swimming lap count, bicycle distance and/or speed, blood pressure, blood glucose, skin conduction, skin and/or body temperature, electromyography, electroencephalography, weight, body fat, caloric intake, nutritional intake from food, medication intake, sleep periods (i.e., clock time), sleep phases, sleep quality and/or duration, pH levels, hydration levels, and respiration rate. The device may also measure or calculate metrics related to the environment around the user such as barometric pressure, weather conditions (for example, temperature, humidity, pollen count, air quality, rain/snow conditions, wind speed), light exposure (for example, ambient light, UV light exposure, time and/or duration spent in darkness), noise exposure, radiation exposure, and magnetic field.

Still further, other metrics can include, without limitation, calories burned by a user (or energy expended), weight gained by a user, weight lost by a user, stairs ascended, e.g., climbed, etc., by a user, stairs descended by a user, steps taken by a user during walking or running, a number of rotations of a bicycle pedal rotated by a user, sedentary activity data, driving a vehicle, a number of golf swings taken by a user, a number of forehands of a sport played by a user, a number of backhands of a sport played by a user, or a combination thereof. In some embodiments, sedentary activity data is referred to herein as inactive activity data or as passive activity data. In some embodiments, when a user is not sedentary and is not sleeping, the user is active. In some embodiments, a user may stand on a monitoring device that determines a physiological parameter of the user. For example, a user stands on a scale that measures a weight, a body fat percentage, a biomass index, or a combination thereof, of the user.

Furthermore, the device or the system collating the data streams may calculate metrics derived from this data. For example, the device or system may calculate the user's stress and/or relaxation levels through a combination of heart rate variability, skin conduction, noise pollution, and sleep quality. In another example, the device or system may determine the efficacy of a medical intervention (for example, medication) through the combination of medication intake, sleep and/or activity data. In yet another example, the device or system may determine the efficacy of an allergy medication through the combination of pollen data, medication intake, sleep and/or activity data. These examples are provided for illustration only and are not intended to be limiting or exhaustive.

This information can be associated to the users account, which can be managed by an activity management application on the server. The activity management application can provide access to the users account and data saved thereon. The activity manager application running on the server can be in the form of a web application. The web application can provide access to a number of websites screens and pages that illustrate information regarding the metrics in various formats. This information can be viewed by the user, and synchronized with a computing device of the user, such as a smart phone.

In one embodiment, the data captured by the activity tracking device 100 is received by the computing device, and the data is synchronized with the activity measured application on the server. In this example, data viewable on the computing device (e.g. smart phone) using an activity tracking application (app) can be synchronized with the data present on the server, and associated with the user's account. In this way, information entered into the activity tracking application on the computing device can be synchronized with application illustrated in the various screens of the activity management application provided by the server on the website.

The user can therefore access the data associated with the user account using any device having access to the Internet. Data received by the network 176 can then be synchronized with the user's various devices, and analytics on the server can provide data analysis to provide recommendations for additional activity, and or improvements in physical health. The process therefore continues where data is captured, analyzed, synchronized, and recommendations are produced. In some embodiments, the captured data can be itemized and partitioned based on the type of activity being performed, and such information can be provided to the user on the website via graphical user interfaces, or by way of the application executed on the users smart phone (by way of graphical user interfaces).

In an embodiment, the sensor or sensors of a device 100 can determine or capture data to determine an amount of movement of the monitoring device over a period of time. The sensors can include, for example, an accelerometer, a magnetometer, a gyroscope, or combinations thereof. Broadly speaking, these sensors are inertial sensors, which capture some movement data, in response to the device 100 being moved. The amount of movement (e.g., motion sensed) may occur when the user is performing an activity of climbing stairs over the time period, walking, running, etc. The monitoring device may be worn on a wrist, carried by a user, worn on clothing (using a clip, or placed in a pocket), attached to a leg or foot, attached to the user's chest, waist, or integrated in an article of clothing such as a shirt, hat, pants, blouse, glasses, and the like. These examples are not limiting to all the possible ways the sensors of the device can be associated with a user or thing being monitored.

In other embodiments, a biological sensor can determine any number of physiological characteristics of a user. As another example, the biological sensor may determine heart rate, a hydration level, body fat, bone density, fingerprint data, sweat rate, and/or a bioimpedance of the user. Examples of the biological sensors include, without limitation, a biometric sensor, a physiological parameter sensor, a pedometer, or a combination thereof.

In some embodiments, data associated with the user's activity can be monitored by the applications on the server and the users device, and activity associated with the user's friends, acquaintances, or social network peers can also be shared, based on the user's authorization. This provides for the ability for friends to compete regarding their fitness, achieve goals, receive badges for achieving goals, get reminders for achieving such goals, rewards or discounts for achieving certain goals, etc.

As noted, an activity tracking device 100 can communicate with a computing device (e.g., a smartphone, a tablet computer, a desktop computer, or computer device having wireless communication access and/or access to the Internet). The computing device, in turn, can communicate over a network, such as the Internet or an Intranet to provide data synchronization. The network may be a wide area network, a local area network, or a combination thereof. The network may be coupled to one or more servers, one or more virtual machines, or a combination thereof. A server, a virtual machine, a controller of a monitoring device, or a controller of a computing device is sometimes referred to herein as a computing resource. Examples of a controller include a processor and a memory device.

In one embodiment, the processor may be a general purpose processor. In another embodiment, the processor can be a customized processor configured to run specific algorithms or operations. Such processors can include digital signal processors (DSPs), which are designed to execute or interact with specific chips, signals, wires, and perform certain algorithms, processes, state diagrams, feedback, detection, execution, or the like. In some embodiments, a processor can include or be interfaced with an application specific integrated circuit (ASIC), a programmable logic device (PLD), a central processing unit (CPU), or a combination thereof, etc.

In some embodiments, one or more chips, modules, devices, or logic can be defined to execute instructions or logic, which collectively can be viewed or characterized to be a processor. Therefore, it should be understood that a processor does not necessarily have to be one single chip or module, but can be defined from a collection of electronic or connecting components, logic, firmware, code, and combinations thereof.

Examples of a memory device include a random access memory (RAM) and a read-only memory (ROM). A memory device may be a Flash memory, a redundant array of disks (RAID), a hard disk, or a combination thereof.

Embodiments described in the present disclosure may be practiced with various computer system configurations including hand-held devices, microprocessor systems, microprocessor-based or programmable consumer electronics, minicomputers, mainframe computers and the like. Several embodiments described in the present disclosure can also be practiced in distributed computing environments where tasks are performed by remote processing devices that are linked through a wire-based or wireless network.

With the above embodiments in mind, it should be understood that a number of embodiments described in the present disclosure can employ various computer-implemented operations involving data stored in computer systems. These operations are those requiring physical manipulation of physical quantities. Any of the operations described herein that form part of various embodiments described in the present disclosure are useful machine operations. Several embodiments described in the present disclosure also relate to a device or an apparatus for performing these operations. The apparatus can be specially constructed for a purpose, or the apparatus can be a computer selectively activated or configured by a computer program stored in the computer. In particular, various machines can be used with computer programs written in accordance with the teachings herein, or it may be more convenient to construct a more specialized apparatus to perform the required operations.

Various embodiments described in the present disclosure can also be embodied as computer-readable code on a non-transitory computer-readable medium. The computer-readable medium is any data storage device that can store data, which can thereafter be read by a computer system. Examples of the computer-readable medium include hard drives, network attached storage (NAS), ROM, RAM, compact disc-ROMs (CD-ROMs), CD-recordables (CD-Rs), CD-rewritables (RWs), magnetic tapes and other optical and non-optical data storage devices. The computer-readable medium can include computer-readable tangible medium distributed over a network-coupled computer system so that the computer-readable code is stored and executed in a distributed fashion.

Although the method operations were described in a specific order, it should be understood that other housekeeping operations may be performed in between operations, or operations may be performed in an order other than that shown, or operations may be adjusted so that they occur at slightly different times, or may be distributed in a system which allows the occurrence of the processing operations at various intervals associated with the processing.

Although the foregoing embodiments have been described in some detail for purposes of clarity of understanding, it will be apparent that certain changes and modifications can be practiced within the scope of the appended claims. Accordingly, the present embodiments are to be considered as illustrative and not restrictive, and the various embodiments described in the present disclosure are not to be limited to the details given herein, but may be modified within the scope and equivalents of the appended claims.

What is claimed is:

1. A method for presenting a message on an activity monitoring device, comprising:
   storing a plurality of messages to a memory of the activity monitoring device, each of the plurality of messages being predefined activity related statements directed to a user of the activity monitoring device, wherein storing the plurality of messages includes identifying the activity monitoring device to a server and downloading the plurality of messages from the server, the server being configured to access a user account associated with the activity monitoring device, the plurality of messages being selected by the server based on the user account;
   detecting a stationary state of the activity monitoring device;
   detecting a movement of the activity monitoring device from the stationary state;
   in response to detecting the movement from the stationary state, selecting one of the plurality of messages from the memory of the activity monitoring device; and
   displaying the selected message on the activity monitoring device;
   wherein selecting one of the plurality of messages includes determining a selection condition that includes one or more of a current date, a location of the activity monitoring device, a current season, or a current weather.

2. The method of claim 1, wherein detecting the stationary state includes detecting non-movement of the activity monitoring device for a predefined time period.

3. The method of claim 1, wherein at least one of the plurality of messages is defined based on an activity history of a user associated with the activity monitoring device.

4. The method of claim 3, wherein the activity history is defined by levels of activity associated to specific time periods.

5. The method of claim 1, wherein the operations of selecting and displaying are not performed during a time period for which an event is scheduled in a calendar of a user of the activity monitoring device.

6. The method of claim 1, wherein the activity monitoring device is configured to detect one or more of the following activities by a user: steps taken, energy consumed, elevation gained, active minutes.

7. The method of claim 1, wherein detecting the stationary state includes detecting a predefined orientation of the activity monitoring device and maintenance of the predefined orientation for a predefined time period.

8. An activity monitoring device, comprising:
a message storage device configured to store a plurality of messages, each of the plurality of messages being predefined activity related statements directed to a user of the activity monitoring device;
a motion sensor;
a display;
logic configured to download the plurality of messages to the message storage device, wherein the downloading includes identifying the activity monitoring device to a server, the server being configured to access a user account associated with the activity monitoring device, the plurality of messages being selected by the server based on the user account;
logic implemented by a circuit configured to detect, based on output of the motion sensor, a stationary state of the activity monitoring device and a subsequent movement of the activity monitoring device from the stationary state, and, in response to detecting the movement from the stationary state, select one of the plurality of messages from the message storage device, and display the selected message on the activity monitoring device;
wherein selecting one of the plurality of messages includes determining a selection condition that includes an activity history of a user associated with the activity monitoring device.

9. The activity monitoring device of claim 8, wherein detecting the stationary state includes detecting non-movement of the activity monitoring device for a predefined time period.

10. The activity monitoring device of claim 8, wherein the selection condition includes one or more of a length of time of the stationary state, a current time of day, a current location of the activity monitoring device, or an activity history associated with a user of the activity monitoring device.

11. The activity monitoring device of claim 8, wherein at least one of the plurality of messages is defined based on one or more of a current date, a location of the activity monitoring device, a current season, or a current weather.

12. The activity monitoring device of claim 8, wherein the activity history is defined by levels of activity associated to specific time periods.

13. The activity monitoring device of claim 8, wherein the activity monitoring device is configured to detect one or more of the following activities by a user: steps taken, energy consumed, elevation gained, active minutes.

14. The activity monitoring device of claim 8, wherein detecting the stationary state includes detecting a predefined orientation of the activity monitoring device and maintenance of the predefined orientation for a predefined time period.

15. A method for presenting a message on an activity monitoring device, comprising:
storing a plurality of messages to a memory of the activity monitoring device, at least one of the plurality of messages defining a statement directed to a user of the activity monitoring device, wherein storing the plurality of messages includes identifying the activity monitoring device to a server and downloading the plurality of messages from the server, the server being configured to access a user account associated with the activity monitoring device, the plurality of messages being selected by the server based on the user account;
detecting a stationary state of the activity monitoring device;
detecting a movement of the activity monitoring device from the stationary state;
in response to detecting the movement from the stationary state, selecting one of the plurality of messages from the memory of the activity monitoring device; and
displaying the selected message on the activity monitoring device;
wherein at least one of the plurality of messages is defined by input received from a secondary user, the secondary user being a member of a social graph of a primary user associated with the activity monitoring device.

16. The method of claim 15, wherein detecting the stationary state includes detecting non-movement of the activity monitoring device for a predefined time period, the non-movement of the activity monitoring device being defined by an absence of movements exceeding a predefined threshold.

17. The method of claim 15, wherein at least one of the plurality of messages is defined based on an activity history of a user associated with the activity monitoring device.

18. The method of claim 17, wherein the activity history is defined by levels of activity associated to specific time periods.

19. The method of claim 15, wherein the operations of selecting and displaying are not performed during a time period for which an event is scheduled in a calendar of a user of the activity monitoring device.

20. The method of claim 15, wherein detecting the stationary state includes detecting a predefined orientation of the activity monitoring device and maintenance of the predefined orientation for a predefined time period.

21. An activity monitoring device, comprising:
a message storage device configured to store a plurality of messages, at least one of the plurality of messages defining a statement directed to a user of the activity monitoring device;
a motion sensor;
a display;
logic configured to download the plurality of messages to the message storage device, wherein the downloading includes identifying the activity monitoring device to a server, the server being configured to access a user account associated with the activity monitoring device, the plurality of messages being selected by the server based on the user account;
a processor configured to detect, based on output of the motion sensor, a stationary state of the activity monitoring device and a subsequent movement of the activity monitoring device from the stationary state, and, in response to detecting the movement from the stationary state, select one of the plurality of messages from the message storage device, and display the selected message on the activity monitoring device, wherein detecting the stationary state includes detecting a predefined orientation of the activity monitoring device;
wherein selecting one of the plurality of messages includes determining a selection condition that includes an activity history of a user associated with the activity monitoring device.

22. The activity monitoring device of claim 21, wherein detecting the stationary state includes detecting maintenance of the predefined orientation of the activity monitoring device for a predefined time period.

23. The activity monitoring device of claim 21, wherein the predefined orientation is defined by a substantially horizontal orientation of a top surface of the activity monitoring device at which the display is defined.

24. The activity monitoring device of claim 21, wherein detecting the stationary state includes detecting one of a plurality of predefined orientations.

25. The activity monitoring device of claim 24, wherein the plurality of predefined orientations are defined by stable orientations of the activity monitoring device on a substantially horizontal surface.

26. The activity monitoring device of claim 21, wherein the stationary state is defined by an absence of movements exceeding a predefined threshold.

27. The activity monitoring device of claim 21,
wherein the selection condition includes one or more of a length of time of the stationary state, a current time of day, a current location of the activity monitoring device; and
wherein at least one of the plurality of messages is defined based on one or more of a current date, a location of the activity monitoring device, a current season, or a current weather.

* * * * *